US011919891B2

(12) United States Patent
Raimundo et al.

(10) Patent No.: US 11,919,891 B2
(45) Date of Patent: *Mar. 5, 2024

(54) BICYCLIC COMPOUNDS USEFUL AS GPR120 MODULATORS

(71) Applicant: Valo Health, Inc., Boston, CA (US)

(72) Inventors: Brian Raimundo, Boston, MA (US); Elena S. Koltun, Boston, MA (US); John Griffin, Boston, MA (US); Eric Stangeland, Boston, MA (US)

(73) Assignee: Valo Health, Inc., Boston, MA (US)

( * ) Notice: Subject to any disclaimer, the term of this patent is extended or adjusted under 35 U.S.C. 154(b) by 1 day.

This patent is subject to a terminal disclaimer.

(21) Appl. No.: 17/121,165

(22) Filed: Dec. 14, 2020

(65) Prior Publication Data

US 2021/0347768 A1 Nov. 11, 2021

Related U.S. Application Data

(63) Continuation of application No. 16/331,928, filed as application No. PCT/US2017/050964 on Sep. 11, 2017, now Pat. No. 10,865,201.

(60) Provisional application No. 62/393,619, filed on Sep. 12, 2016.

(51) Int. Cl.
| *C07D 417/12* | (2006.01) |
| *A61P 1/16* | (2006.01) |
| *A61P 3/08* | (2006.01) |
| *A61P 3/10* | (2006.01) |
| *A61P 25/28* | (2006.01) |
| *A61P 29/00* | (2006.01) |
| *C07D 275/06* | (2006.01) |
| *C07D 401/12* | (2006.01) |
| *C07D 417/14* | (2006.01) |

(52) U.S. Cl.
CPC .............. *C07D 417/12* (2013.01); *A61P 1/16* (2018.01); *A61P 3/08* (2018.01); *A61P 3/10* (2018.01); *A61P 25/28* (2018.01); *A61P 29/00* (2018.01); *C07D 275/06* (2013.01); *C07D 401/12* (2013.01); *C07D 417/14* (2013.01)

(58) Field of Classification Search
CPC .. C07D 275/06; C07D 401/12; C07D 417/14; A61P 3/08; A61P 29/00
See application file for complete search history.

(56) References Cited

U.S. PATENT DOCUMENTS

| 2,735,225 | A | 2/1956 | Goodhue et al. |
| 5,334,600 | A | 8/1994 | Van Duzer et al. |
| 5,350,761 | A | 9/1994 | Van Duzer et al. |
| 5,411,978 | A | 5/1995 | Ladislas et al. |
| 6,716,836 | B2 | 4/2004 | Ogilvie et al. |
| 8,110,681 | B2 | 2/2012 | Heemskerk et al. |
| 9,562,053 | B2 | 2/2017 | Sui et al. |
| 10,800,773 | B2 * | 10/2020 | Raimundo ................. A61P 3/10 |
| 10,865,201 | B2 * | 12/2020 | Raimundo ........... C07D 417/12 |
| 11,548,886 | B2 * | 1/2023 | Raimundo ............... A61P 25/16 |
| 2009/0275578 | A1 | 11/2009 | Clayton et al. |
| 2010/0035944 | A1 | 2/2010 | Epple et al. |
| 2010/0063025 | A1* | 3/2010 | Plettenburg ............... A61P 1/16 |
| | | | 540/597 |
| 2011/0245247 | A1 | 10/2011 | Braje et al. |
| 2011/0312976 | A1 | 12/2011 | Arakawa et al. |
| 2011/0313003 | A1 | 12/2011 | Shi et al. |
| 2014/0275182 | A1 | 9/2014 | Sui et al. |
| 2015/0274672 | A1 | 10/2015 | Chelliah et al. |
| 2015/0291527 | A1 | 10/2015 | Kim et al. |
| 2015/0322044 | A1 | 11/2015 | Jurica et al. |
| 2015/0336974 | A1 | 11/2015 | Youngman |
| 2019/0047990 | A1 | 2/2019 | Berdini et al. |
| 2019/0202821 | A1 | 7/2019 | Raimundo et al. |

FOREIGN PATENT DOCUMENTS

| CN | 101500995 A | 8/2009 |
| CN | 105209444 A | 12/2015 |
| DE | 22 53 251 A1 | 5/1974 |
| EP | 0 145 078 A2 | 6/1985 |
| EP | 0 526 402 A1 | 2/1993 |
| EP | 0 548 934 A1 | 6/1993 |
| EP | 2 172 198 A1 | 4/2010 |
| JP | H641104 A | 2/1994 |
| JP | 2004-523590 A | 8/2004 |
| JP | 2014-533736 A | 12/2014 |
| JP | 2016-141618 A | 8/2016 |
| WO | WO-96/26195 A1 | 8/1996 |
| WO | WO-97/36871 A1 | 10/1997 |
| WO | WO-02/076982 A2 | 10/2002 |
| WO | WO-03/033480 A1 | 4/2003 |
| WO | WO-2005/037779 A2 | 4/2005 |
| WO | WO-2006/020879 A1 | 2/2006 |

(Continued)

OTHER PUBLICATIONS

Choi, et al., "Synthesis of aristolactam analogues and evaluation of their antitumor activity", Bioorganic & Medicinal Chemistry Letters, vol. 19, No. 11, Apr. 10, 2009, pp. 3036-3040.
Extended European Search Report dated Mar. 30, 2020, from application No. 17849722.8.
Fells, et al., "2D binary QSAR modeling of LPA3 receptor antagonism", Journal of Molecular Graphics and Modelling, vol. 28, No. 8, Jun. 1, 2010, pp. 828-833.
Fells, et al., "Structure-based drug design identifies novel LPA3 antagonists", Bioorganic & Medicinal Chemistry, vol. 17, No. 21, Nov. 1, 2009, pp. 7457-7464.
Fuccella, et al., "Fate of the Analgesic and Anti-Inflammatory Drug K 4277 after Oral Administration to Man", European Journal of Clinical Pharmacology, vol. 6, No. 4, Dec. 1, 1973, pp. 256-260.
Golbraikh, et al., "Validation of protein-based alignment in 3D quantitative structure-activity relationships with CoMFA models", European Journal of Medicinal Chemistry, vol. 35, No. 1, Jan. 1, 2000, pp. 123-136.

(Continued)

*Primary Examiner* — Daniel R Carcanague
(74) *Attorney, Agent, or Firm* — Foley & Lardner LLP

(57) ABSTRACT

Provided herein are compounds, compositions including them, and methods of modulating GPR120 activity and treating diseases mediated by GPR120 by administering such compounds and compositions.

20 Claims, 2 Drawing Sheets

(56) References Cited

FOREIGN PATENT DOCUMENTS

| WO | WO-2006/038594 A1 | 4/2006 | |
|---|---|---|---|
| WO | WO-2007/109211 A2 | 9/2007 | |
| WO | WO-2007109211 A2 * | 9/2007 | ............. A61P 13/12 |
| WO | WO-2010/048207 A2 | 4/2010 | |
| WO | WO-2010/080537 A1 | 7/2010 | |
| WO | WO-2010/104195 A1 | 9/2010 | |
| WO | WO-2011/159297 A1 | 12/2011 | |
| WO | WO-2013/011402 A1 | 1/2013 | |
| WO | WO-2013/079452 A1 | 6/2013 | |
| WO | WO-2014/086663 A1 | 6/2014 | |
| WO | WO-2014/096941 A1 | 6/2014 | |
| WO | WO-2014/209034 A1 | 12/2014 | |
| WO | WO-2015/150565 A1 | 10/2015 | |
| WO | WO-2016/033436 A1 | 3/2016 | |

OTHER PUBLICATIONS

Hussein, et al., "Synthesis and Structural Investigation of N-Pyridyl-1, 3-Dihydroxyisoindolines", Asian Journal of Chemistry, vol. 3, No. 1, Jan. 1, 1991, pp. 30-37.

International Preliminary Report on Patentability dated Oct. 2, 2018, from application No. PCT/US2017/050964.

International Search Report and Written Opinion dated Nov. 21, 2017, from application No. PCT/US2017/050964.

International Search Report and Written Opinion dated Nov. 27, 2017, from application No. PCT/US2017/050956.

Ke, et al., "Ligand efficiency based approach for efficient virtual screening of compound libraries", European Journal of Medicinal Chemistry, (2014), 83, pp. 226-235.

Kita, et al., "Thymidine Phosphorylase Inhibitors with a Homophthalimide Skeleton", Biol. Pharm. Bull. 24(7) 860-862 (2001).

Liu, et al., "FFA4 receptor (GPR120): A hot target for the development of anti-diabetic therapies", European Journal of Pharmacology, 763, 2015, pp. 160-168.

Lorion, et al., "Complementary Synthetic Approaches to Constitutionally Diverse N-Amino-alkylated Isoindolinones: Application to the Synthesis of Falipamil and 5-HT1A Receptor Ligand Analogues", Synthesis, vol. 2009, No. 11, Apr. 14, 2009, pp. 1897-1903.

Lorion, et al., "Cyclic Sulfamidates as Vehicles for the Synthese of Poly- and Diversely Substituted Benzosultams via Unusual S(O)2-O Bond Cleavage", Organic Letters, 2010, vol. 12, No. 6, pp. 1356-1359.

Mancilla-Percino, et al., "Isoindoline Derivatives of alpha-Amino Acids as Cyclooxygenase 1 and 2 Inhibitors," Arch. Pharm. Chem. Life Sci., 2016, 349, pp. 175-185.

Murray, et al., "The Electron Capture Negative Ion Chemical Ionization Mass Spectra of 2-(4',6'- Bistrifluoromethyl-2'-pyrimidinyl)-tetrahydroisoquinoline and 4-Substituted Analogues," Biomedical Spectrometry (1982), 9(11), pp. 466-472.

National Center for Biotechnology Information. PubChem Database. SR-05000020926, Source=The Scripps Research Institute Molecular Screening Center, SID=174009379, https://pubchem.ncbi.nlm.nih.gov/substance/174009379 (accessed on Feb. 11, 2020). Available on Mar. 21, 2015 , 7 pages.

Non-Final Office Action dated Nov. 4, 2019, from U.S. Appl. No. 16/331,916.

Norcross, et al., "Trisubstituted Pyrimidines as Efficacious and Fast-Acting Antimalarials", Journal of Medicinal Chemistry, vol. 59, No. 13, Jun. 17, 2016, pp. 6101-6120.

Notice of Allowance dated Feb. 10, 2020, from U.S. Appl. No. 16/331,916.

Notice of Allowance dated Jul. 29, 2020, from U.S. Appl. No. 16/331,928.

Registry (STN) D 1935530-23-6 [online], Oct. 7, 2011-Jun. 20, 2016 [date of retrieval: Mar. 1, 2021], (2011).

RN: 1334634 35 3, Chemical Abstracts Service, STN Registry, Oct. 7, 2011, (2011).

RN: 1440520-62-6, Chemical Abstracts Service, STN Registry, Jun. 24, 2013, (2013).

RN: 1935530-23-6 Chemical Abstracts Service, STN Registry Jun. 20, 2016, (2016).

Sabatucci, et al., "Substituted 4-hydroxyphenyl sulfonamides as pathway-selective estrogen receptor ligands", Bioorganic & Medicinal Chemistry Letters 16 (2006) 854-858.

Selvakumar, et al., "Synthesis of Condensed Tetrahydroisoquinoline Class of Alkaloids by Employing TfOH-Mediated Imide Carbonyl Activation", European Journal of Organic Chemistry, vol. 2015, No. 10, Apr. 1, 2015, pp. 2175-2188.

Song, et al., "Design, Synthesis, and Preliminary Activity Evaluation of Novel Pyrimidine Derivatives as Acid Pump Antagonists", Chem Biol Drug Des 2015; 85: pp. 306-314.

Sparks, et al., "Identification of diarylsulfonamides as agonists of the free fatty acid receptor 4 (FFA4/GPR120)", Bioorganic & Medicinal Chemistry Letters, vol. 24, Issue 14, Jul. 15, 2014, pp. 3100-3103.

STN Registry Database, Record for Registry No. RN 1252377-76-6, Entered into STN on Nov. 10, 2010, 1 page.

Talukdar, et al., "Targeting GPR120 and other fatty acid-sensing GPCRs ameliorates insulin resistance and inflammatory diseases", Trends in Pharmacological Sciences, Sep. 2011, vol. 32, No. 9, pp. 543-550.

U.S. Final Office Action dated Mar. 20, 2020, from U.S. Appl. No. 16/331,928.

U.S. Non-Final Office Action dated Sep. 9, 2019, from U.S. Appl. No. 16/331,928.

Witty, et al., "Discovery of potent and stable conformationally constrained analogues of the MCH R1 antagonist SB-568849", Bioorganic & Medicinal Chemistry Letters, vol. 16, No. 18, Jul. 12, 2006, pp. 4872-4878.

Tao et al., "Diastereoselective Synthesis of 1,3-disubstituted Isoindolines and Sultams via Bronsted Acid Catalysis", Chem. Commun., 2018, 54, pp. 11292-11295.

* cited by examiner

BICYCLIC COMPOUNDS USEFUL AS GPR120 MODULATORS

CROSS-REFERENCE TO RELATED APPLICATIONS

This application is a continuation of U.S. application Ser. No. 16/331,928, filed Mar. 8, 2019, now U.S. Pat. No. 10,865,201, issued Dec. 15, 2020, which is a national stage entry under 35 U.S.C. § 371 of International Application No. PCT/US2017/050964, filed Sep. 11, 2017, which in turn claims priority from Provisional U.S. Application Ser. No. 62/393,619, filed Sep. 12, 2016, the contents each of which are hereby incorporated herein by reference in their entireties entirety.

FIELD OF THE INVENTION

The present invention provides compositions and methods for modulating the GPR120 receptor, and generally relates to the fields of medicinal chemistry, medicine, pharmacology, molecular biology, and biology. Compounds modulating the GPR120 receptor are useful for treating various metabolic and inflammatory diseases, including but not limited to, type 2 diabetes, obesity, hepatic steatosis, and Alzheimer's, and one or more symptoms of each thereof.

BACKGROUND OF THE INVENTION

Type 2 diabetes (T2D) is a chronic disease resulting from the body's inefficient use of the insulin it produces. The states of hyperglycemia and insulin resistance observed in T2D typically result from excess weight and lack of physical exercise. Because obesity and sedentary lifestyles are increasing worldwide, the incidence of T2D is also rapidly increasing. The World Health Organization (WHO) estimates that more than 300 million people worldwide have T2D, and that more than 1 million deaths per year can be directly attributed to T2D. WHO furthermore projects that diabetes-associated deaths will increase by 50% over the next decade. Current therapeutic strategies for T2D include treatment with agents that target the secretion or utilization of insulin. However, these strategies do not work or do not work well for all patients, and new strategies and agents are needed for treatment of the multiple aspects of T2D pathology.

GPR120, also known as free fatty acid receptor 4 (FFA4), is a 7-transmembrane-spanning G-protein coupled receptor that is activated by long-chain free fatty acids including the ω-3 fatty acids. GPR120 is expressed in a wide range of tissues and mediates multiple effects associated with energy balance and inflammation. In enteroendocrine cells, activation of GPR120 leads to secretion of the incretins glucagon-like peptide-1 (GLP-1) and gastric inhibitory peptide (GIP), which in turn stimulate release of insulin from pancreatic beta cells. Activation of GPR120 in adipocytes stimulates glucose uptake and adipogenesis while inhibiting lipolysis. Activation of GPR120 in macrophages exerts anti-inflammatory effects, inhibiting the release of cytokines including TNF-α and IL-6. In enteroendocrine cells and adipocytes, GPR120 signaling proceeds through Gq/11, but in macrophages GPR120 signaling proceeds through the β-arrestin pathway. Dysfunction in GPR120 has been associated with diabetes and obesity in both mice and humans. Accordingly, GPR120 agonists have been tested for the treatment of T2D and other metabolic diseases.(1-4)

Hepatic steatosis is a state of inflammation and cell injury associated with the accumulation of fat in the liver. In cases not related to alcohol intake, the disease is known as non-alcoholic steatohepatitis (NASH). NASH is increasingly common, can lead to liver cirrhosis or liver failure, and is often observed in people with obesity, glucose intolerance, or dyslipidemia. Recent studies utilizing wild type and GPR120 deficient mice confirm a positive role for GPR120 in controlling lipid metabolism, triglyceride and diacylglycerol levels, and inflammatory markers. Consistent with these results, a study of children with nonalcoholic fatty liver disease who were treated with the GPR120 agonist docosahexaenoic (DHA) acid resulted in reduced liver damage and inflammatory macrophages, and increased GPR120 hepatocyte expression.(5a).

Alzheimer's disease (AD) is the most common cause of dementia in the elderly, with an estimated 47M cases worldwide at present and an expectation for more than 130M cases by 2050. Recently it has been demonstrated that activation of GPR120 exerts anti-inflammatory effects in immortalized hypothalamic neurons,(6a) and that GPR120 and another long chain free fatty acid receptor, GPR40 (FFA1), control energy homeostasis and inflammation in the mouse hypothalamus (7a). NLRP3 inflammasome activity has been shown to contribute to pathology in APP/PS1 mice (8a). Omega-3 fatty acids block activation of NLRP3 inflammasomes in macrophages, thereby inhibiting downstream activation of caspase-1 and maturation and release of interleukin-1beta (IL-1beta) (9a). Expression of NLRP1 inflammasomes is also upregulated in the brains of APP/PS1 mice, and Aβ induces NLRP1- and caspase-1 dependent pyroptosis in cultured cortical neurons from these animals (10a). Levels of inflammasome-activated caspase-1 are strongly enhanced in the brains of humans with mild cognitive impairment and AD, and activation of NLRP1 in cultured human neurons induces axonal degeneration (11a). Accordingly, GPR120 agonists hold promise as disease-modifying therapeutics for AD, Parkinson's disease, frontotemporal dementia (FTD), amyotrophic lateral sclerosis (ALS), multi-system atrophy (MSA) and other disorders associated with neuroinflammation.

The present invention provides novel compounds, compositions of matter, particularly pharmaceutical compositions, methods for the synthesis or preparation of the compounds and compositions, and methods for using them to modulate GPR120 and treat T2D, hepatic steatosis, Alzheimer's, and other disease associated with metabolic dysfunction and inflammation.

SUMMARY OF THE INVENTION

The present invention provides, in certain aspects, compounds, compositions of matter (particularly pharmaceutical compositions), methods for the synthesis or preparation of the compounds and compositions, and methods for using them to modulate GPR120.

Provided herein are compounds, compositions including them, and methods of modulating the GPR120 receptor and treating diseases by administering such compounds and compositions.

The first aspect of the present invention provides compounds of Formula I that in various embodiments comprise a bicyclic core element containing from 9-10 ring atoms, 1-4 ring nitrogen atoms, and up to 3 ring substituents:

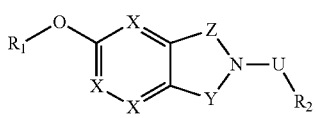

as well as tautomers, isotopomers and stereoisomers thereof, and prodrugs of any of the foregoing, and pharmaceutically acceptable salts and solvates of all of the foregoing, wherein each X independently is CH, CR$_3$, or N; Y is SO$_2$, or CO; Z is —CH$_2$—, —CH(CH$_3$)—, —C(CH$_3$)$_2$—, —C(CH$_2$CH$_2$)—, CO, —(CO)CH$_2$—, —CH$_2$CH$_2$—, or —CHCH—; U is a covalent bond, CH$_2$, —CH(CH$_3$)—, —C(CH$_3$)$_2$—, or —CH$_2$CH$_2$—; R$_1$ is an optionally substituted alkyl group, an optionally substituted 3-7 membered cycloalkyl or heterocyclyl group, an optionally substituted 5- or 6-membered aryl or heteroaryl group, or an optionally substituted 5,6- or 6,6-bicyclic aryl or heteroaryl group; R$_2$ is hydrogen, an optionally substituted 3-7 membered cycloalkyl or heterocyclyl group, an optionally substituted 6-membered aryl group, an optionally substituted 5- or 6-membered heteroaryl group, an optionally substituted 5,6- or 6,6-bicyclic heteroaryl group, or an optionally substituted bicyclic aryl group; R$_3$ is a halogen, or an optionally substituted alkyl or alkoxy group.

The compounds of Formula I are contemplated to be GPR120 agonists that stimulate release of GLP-1, GIP and/or glucagon, inhibit release of ghrelin, stimulate glucose uptake and/or exert anti-inflammatory effects, and thereby exert therapeutic effects in T2D. In another aspect, provided herein is a method for agonizing GPR120, comprising contacting the GPR120 with a compound or the composition provided or disclosed herein.

In another aspect, provided herein is a method for modulating metabolism in a mammal, comprising contacting GPR120 in the mammal with an amount of the compound provided herein that is effective to modulate metabolism in the mammal. In another aspect, provided herein is a method for modulating metabolism in a mammal, comprising administering to the mammal an amount of the composition provided herein that is effective to modulate metabolism in the mammal.

In another aspect, provided herein is a method for reducing inflammation in a mammal, comprising contacting GPR120 in the mammal with an amount of the compound provided herein that is effective to reduce the inflammation. In another aspect, provided herein is a method for reducing inflammation in a mammal, comprising administering to the mammal an amount of the composition provided herein that is effective to reduce the inflammation.

In another aspect, provided herein is a method for reducing neuroinflammation in a mammal, comprising contacting GPR120 in the mammal with an amount of the compound provided herein that is effective to reduce the neuroinflammation. As used herein, neuroinflammation refers to inflammation of the nervous tissue. In another aspect, provided herein is a method for reducing neuroinflammation in a mammal, comprising administering to the mammal an amount of the composition provided herein that is effective to reduce neuroinflammation.

In another aspect, provided herein is a method for treating diabetes, pre-diabetes or metabolic syndrome, or one or more symptoms of each thereof in a mammal, comprising contacting GPR120 in the mammal with a therapeutically effective amount of the compound provided herein. In another aspect, provided herein is a method for treating diabetes, pre-diabetes or metabolic syndrome, or one or more symptoms of each thereof in a mammal, comprising administering to the mammal a therapeutically effective amount of the composition provided herein.

In another aspect, provided herein is a method for treating steatohepatitis in a mammal, comprising contacting GPR120 in the mammal with a therapeutically effective amount of the compound provided herein. In another aspect, provided herein is a method for treating steatohepatitis in a mammal, comprising administering to the mammal a therapeutically effective amount of the composition provided herein.

In another aspect, provided herein is a method for treating non-alcoholic steatohepatitis in a mammal, comprising contacting GPR120 in the mammal with a therapeutically effective amount of the compound provided herein. In another aspect, provided herein is a method for treating non-alcoholic steatohepatitis in a mammal, comprising administering to the mammal a therapeutically effective amount of the composition provided herein.

In another aspect, provided herein is a method for treating a disorder associated with, leading to, or resulting from neuroinflammation in a mammal, comprising contacting GPR120 in the mammal with a therapeutically effective amount of the compound provided herein. In another aspect, provided herein is a method for treating a disorder associated with leading to, or resulting from neuroinflammation in a mammal, comprising administering to the mammal a therapeutically effective amount of the composition provided herein.

In another aspect, provided herein is a method for treating Alzheimer's disease, Parkinson's disease, frontotemporal dementia, amyotrophic lateral sclerosis or multi-system atrophy, or one or more symptoms of each thereof, comprising contacting GPR120 in the patient with a therapeutically effective amount of the compound provided herein.

In another aspect, provided herein is a method for treating Alzheimer's disease, Parkinson's disease, frontotemporal dementia, amyotrophic lateral sclerosis or multi-system atrophy, or one or more symptoms of each thereof, comprising administering to the patient a therapeutically effective amount of the composition provided herein.

DETAILED DESCRIPTION OF THE INVENTION

Figure 1:
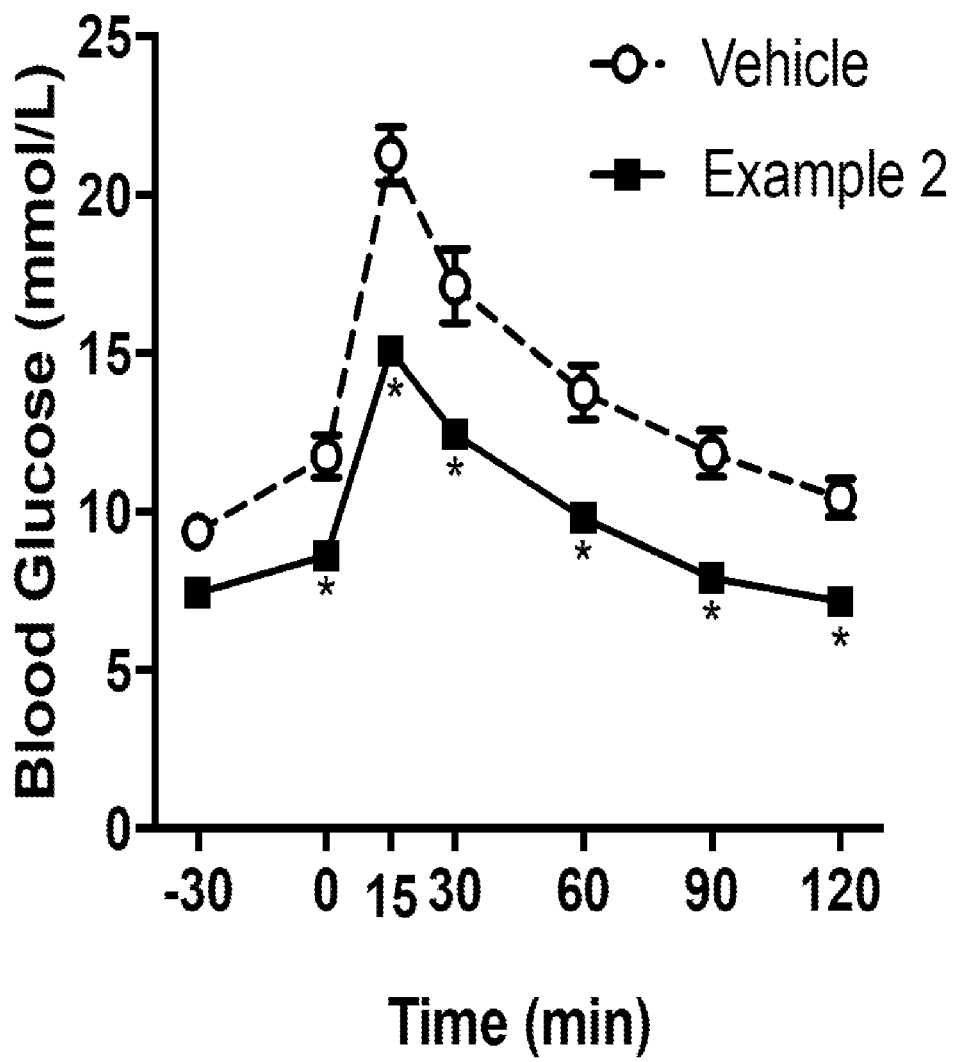
FIG. 1 shows anti-inflammatory activity in LPS-stimulated human peripheral blood mononuclear cells.
Figure 2:
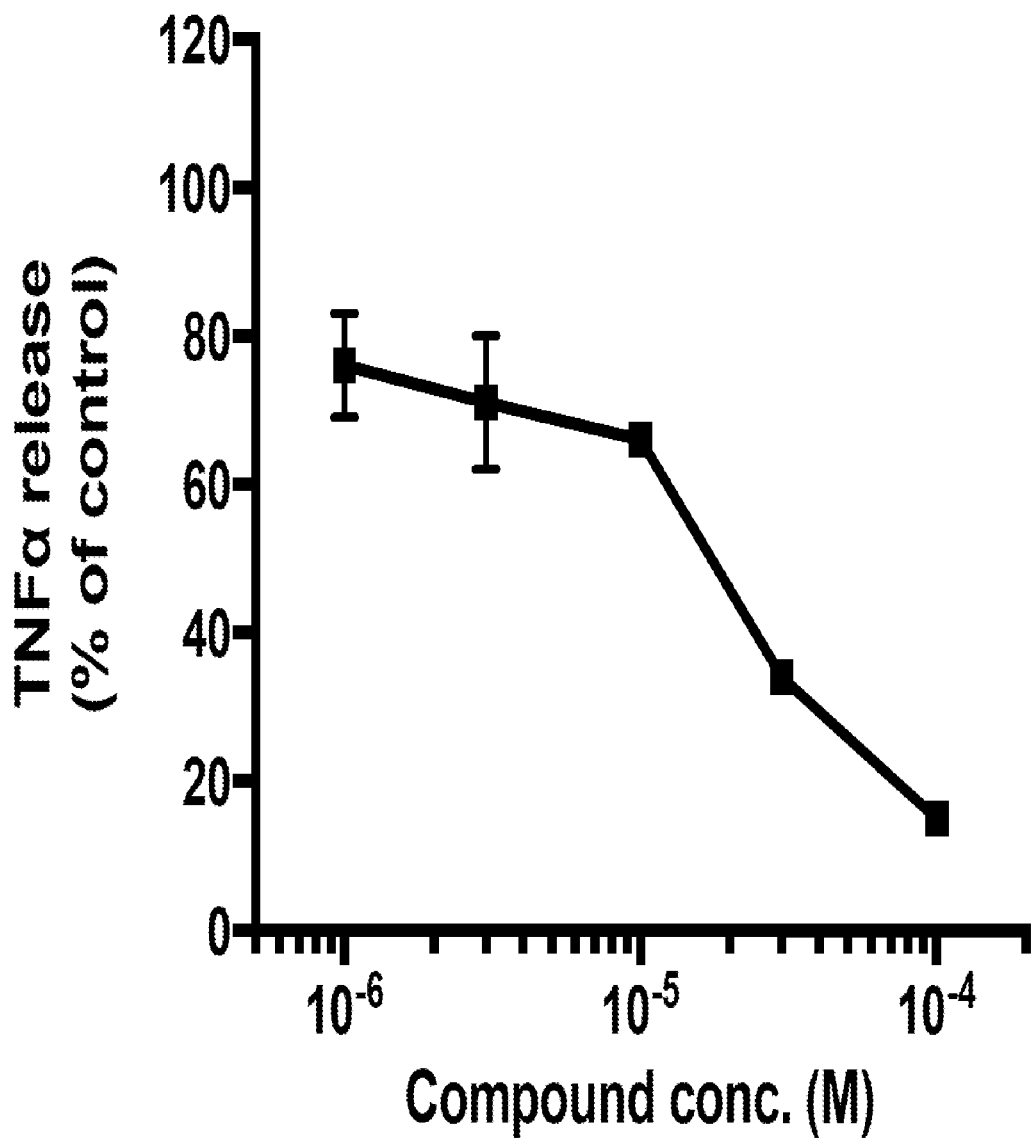
FIG. 2 shows TNFα release reported as % of vehicle treated LPS stimulated cells as a function of compound concentration.

To aid the reader in understanding the invention, how it is made and used, and the benefits thereof, the following usages and definitions are provided.

All numerical designations, e.g., pH, temperature, time, concentration, and molecular weight, including ranges, are approximations which may be varied (+) or (−) by increments of, e.g., 0.1 or 1. Thus, all numerical designations may be interpreted by the reader as preceded by the term "about". Similarly, the reagents described herein are merely exemplary; generally, the artisan of ordinary skill will appreciate that equivalents of such are known in the art. As used in the specification and claims, the singular forms "a", "an" and "the" should be interpreted as inclusive of plural references unless the context clearly dictates otherwise.

"Acyl" refers to a group of formula —CO—$R_x$ wherein $R_x$ is H, or is optionally substituted alkyl, cycloalkyl, heterocyclyl, aryl, or heteroaryl. Examples of acyl groups include, for example, —CHO, —CO-Me, and —CO-Ph.

"Administering" or "administration of" a compound or composition drug to a patient (and grammatical equivalents of this phrase) refers to direct administration, which may be administration to a patient by a medical professional or may be self-administration, and/or indirect administration, which may be the act of prescribing a drug. For example, a physician who instructs a patient to self-administer a drug and/or provides a patient with a prescription for a drug is administering the drug to the patient.

"Alkoxy" refers to an alkyl group covalently bonded to an oxygen atom. In other words, an alkoxy group has the general structure —O-alkyl. $C_1$-$C_6$ alkoxy groups include, for example, methoxy, ethoxy, propoxy, isopropoxy, n-butoxy, sec-butoxy, tert-butoxy, n-pentoxy, 2-pentoxy, 3-pentoxy, isopentoxy, neopentoxy, hexoxy, 2-hexoxy, 3-hexoxy, and 3-methylpentoxy.

"Alkenyl" refers to a straight (or linear) or branched chain hydrocarbon group containing at least one carbon-carbon double bond. $C_1$-$C_6$ alkenyl groups include, for example, vinyl, allyl, and butenyl.

"Alkyl" refers to a straight (or linear) or branched chain hydrocarbon group. $C_1$-$C_6$ alkyl groups include, for example, methyl, ethyl, propyl, isopropyl, n-butyl, sec-butyl, tert-butyl, pentyl, 2-pentyl, isopentyl, neopentyl, hexyl, 2-hexyl, 3-hexyl and 3-methylpentyl.

"Amino" refers to a monovalent radical —$NR^aR^b$ wherein $R^a$ and $R^b$ are independently hydrogen, alkyl, aryl or heteroaryl. The term "alkylamino" refers to the group —$NR^aR^b$ where $R^a$ is alkyl and $R^b$ is H or alkyl. For dialkylamino groups, the alkyl portions can be the same or different and can also be combined to form a 3- to 8-membered ring with the nitrogen atom to which each is attached. Accordingly, a group represented as —$NR^aR^b$ is meant to include heterocyclyl groups such as piperidinyl, pyrrolidinyl, morpholinyl, azetidinyl and the like.

"Aryl" refers to a cyclic moiety that includes one or more monocyclic or fused ring aromatic systems containing from 6-20 ring carbon atoms. Such moieties include any moiety that has one or more monocyclic or bicyclic fused ring aromatic systems, including but not limited to phenyl and naphthyl.

"($C_m$-$C_n$), $C_m$—$C_n$, or $C_m$-n" refer to the number of carbon atoms in a certain group before which one of these symbols are placed. For example, $C_1$-$C_6$ alkyl refers to an alkyl group containing from 1 to 6 carbon atoms.

"Carboxamide or carboxamido" refers to a monovalent radical —CO—$NR^aR^b$, wherein NRaRb is an "amino" group as defined above.

"Carrier" refers to a solid or liquid substance such as a polymer, solvent, suspending agent, absorbing agent, or adsorbing agent for the pre-delivery or capture of a compound of this invention for subsequent delivery. The carrier may be liquid or solid and is selected with the planned manner of administration in mind.

"Comprising" when used to define compounds, compositions and methods means that the recited elements may be present with other materials or steps. "Consisting essentially of," when used to define compounds, compositions or methods, means that the recited elements may not be present with other elements that would materially affect the basic and novel characteristics of the claimed invention. "Consisting of," means only the recited elements.

Embodiments defined by each of these transition terms are within the scope of this invention. "Cycloalkyl" refers to, unless otherwise stated, cyclic versions of "alkyl", "alkenyl" and "alkynyl" in which all ring atoms are carbon. "Cycloalkyl" refers to a mono- or polycyclic group. "Cycloalkyl" may form a bridged ring or a spiro ring. The cycloalkyl group may have one or more double or triple bond(s). Typical cycloalkyl groups have from 3 to 8 ring atoms. Examples of cycloalkyl include cyclopentyl, cyclohexyl, 1-cyclohexenyl, 3-cyclohexenyl, and cycloheptyl.

"Halogen"or halo" refers to by themselves or as part of another substituent, unless otherwise stated, a fluorine, chlorine, bromine, or iodine atom.

"Heteroaryl" refers to a monocyclic aromatic system having 5 or 6 ring atoms, or a fused ring bicyclic aromatic system having 8-20 atoms, in which the ring atoms are C, O, S, SO, $SO_2$, or N, and at least one of the ring atoms is a heteroatom, i.e., O, S, SO, $SO_2$, or N. Heteroaryl groups include, for example, acridinyl, azocinyl, benzimidazolyl, benzofuranyl, benzothio-furanyl, benzothiophenyl, benzoxazolyl, benzothiazolyl, benzotriazolyl, benzotetrazolyl, benzisoxazolyl, benzisothiazolyl, benzimidazolinyl, carbazolyl, NH-carbazolyl, carbolinyl, chromanyl, chromenyl, cinnolinyl, dithiazinyl, furanyl, furazanyl, imidazolidinyl, imidazolinyl, imidazolyl, indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, naphthyridinyl, octahydroisoquinolinyl, oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazole, pyridinyl, pyridyl, pyrimidinyl, pyrrolyl, quinazolinyl, quinolinyl, quinoxalinyl, quinuclidinyl, tetrahydroisoquinolinyl, tetrahydroquinolinyl, tetrazolyl, thiadiazinyl, thiadiazolyl, thianthrenyl, thiazolyl, thienyl, thienothiazolyl, thienooxazolyl, thienoimidazolyl, thiophenyl, triazinyl and xanthenyl. Unless indicated otherwise, the arrangement of the heteroatoms within the ring may be any arrangement allowed by the bonding characteristics of the constituent ring atoms.

"Heterocyclyl" or heterocyclic refers to a monocyclic or fused ring multicyclic cycloalkyl group at least a portion of which is not aromatic and in which one or more of the carbon atoms in the ring system is replaced by a heteroatom selected from O, S, SO, $SO_2$, P, or N. Examples of heterocyclyl groups include but are not limited to imidazolinyl, morpholinyl, piperidinyl, piperidin-2-onyl, piperazinyl, pyrrolidinyl, pyrrolidine-2-onyl, tetrahydrofuranyl, tetrahydropyranyl, and tetrahydroimidazo [4,5-c] pyridinyl.

"Pharmaceutically acceptable salts" refers to salts of the active compounds which are prepared with relatively non-toxic acids or bases, depending on the particular acidic or basic nature of the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, lithium, magnesium, potassium, sodium, and the like. Salts derived from pharmaceutically-acceptable organic bases include salts of primary, secondary and tertiary amines, including substituted amines, cyclic amines, naturally-occurring amines and the like, such as arginine, betaine, caffeine, choline, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginine and the like, and salts of organic acids like glucuronic or galactunoric acids. Certain specific compounds of the present invention may contain both basic and acidic functionalities that allow the compounds to be converted into either base or acid addition salts.

"Pharmaceutically acceptable excipient, carrier, or diluent" refers to an excipient, carrier, or diluent that is useful in preparing a pharmaceutical composition that is generally safe, non-toxic and neither biologically nor otherwise undesirable, and includes an excipient, carrier, or diluent that is acceptable for human pharmaceutical use as well as veterinary use. A "pharmaceutically acceptable excipient, carrier, or diluent" includes both one and more than one such excipient, carrier, or diluent.

"Reduction" or "inhibition" of a symptom or symptoms (and grammatical equivalents of this phrase) of a pathological condition or disease refers to decreasing the severity or frequency of the symptom(s), or elimination of the symptom(s).

"Subject," used herein interchangeably with "individual" and "patient," refers to a vertebrate, typically a mammal, and usually a human. Mammals include, but are not limited to, mice, rats, rabbits, simians, bovines, ovines, porcines, canines, felines, farm animals, sport animals, pets, equines, and primates.

"Substituted" refers to a group as defined herein in which one or more bonds to a carbon(s) or hydrogen(s) are replaced by a bond to non-hydrogen and non-carbon atom "substituents" include, but are not limited to, a halogen atom; an oxygen atom in groups such as hydroxyl groups, alkoxy groups, aryloxy, and acyloxy groups; a sulfur atom in groups such as thiol groups, alkyl and aryl sulfide groups, sulfone groups, sulfonyl groups, and sulfoxide groups; a nitrogen atom in groups such as nitro, —$NH_2$, alkylamines, dialkylamines, arylamines, alkylarylamines, diarylamines, alkoxyamino, hydroxyamino, acylamino, sulfonylamino, N-oxides, imides, and enamines; and other heteroatoms in various other groups. "Substituents" also include groups in which one or more bonds to a carbon(s) or hydrogen(s) atom is replaced by a higher-order bond (e.g., a double- or triple-bond) to a heteroatom such as oxygen in oxo, acyl, amido, alkoxycarbonyl, aminocarbonyl, carboxyl, and ester groups; nitrogen in groups such as imines, oximes, hydrazones, and nitriles. "Substituents" further include groups in which one or more bonds to a carbon(s) or hydrogen(s) atoms is replaced by a bond to a cycloalkyl, heterocyclyl, aryl, and heteroaryl groups. For cycloalkyl, heterocyclyl, aryl, and heteroaryl groups, "substituents" still further include, substituted and unsubstituted alkyl groups. Other substituents include ethynyl, vinyl, carboxyl and its esters and amides, hydroxymethyl, and methyl. Another "substituent" is the trifluoromethyl or other fluoroalkyl group and other groups that contain these groups. Two substituents on same or adjacent carbon atoms may together with the carbon atoms to which they are bonded form a heterocyclic or cycloalkyl group. Typically, a particular group may have 0 (unsubstituted), 1, 2 or 3 substituents. As will be apparent to the skilled artisan, substitutions with substituents will not result in polymeric moieties of greater than 1000 molecular weight.

"Sulfonamide or sulfonamido" refers to a monovalent radical —SO—$NR^aR^b$, wherein NRaRb is an "amino" group as defined above.

"Therapeutically effective amount" is an amount administered to a patient with a disease mediated by GPR120 that is sufficient to effect beneficial or desired results. A therapeutically effective amount can be administered in one or more administrations, applications, or dosages.

"Treating" or "treatment of" a condition or patient refers to taking steps to obtain beneficial or desired results, including clinical results such as the reduction of symptoms. For purposes of this invention, beneficial or desired clinical results include, but are not limited to, alleviation or amelioration of one or more symptoms of diseases mediated by GPR120; diminishment of extent of such diseases; delay or slowing of such disease progression; amelioration, palliation, or stabilization of such diseases; or other beneficial results.

Accordingly, in a first aspect, the invention provides compounds of Formula I.

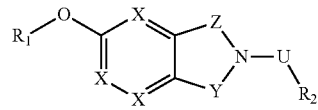

Formula I or tautomers, isotopomers and stereoisomers thereof, and prodrugs of any of the foregoing, and pharmaceutically acceptable salts and solvates of all of the foregoing, wherein X is CH, $CR_3$, or N; Y is $SO_2$, or CO; Z is —$CH_2$—, —$CH(CH_3)$—, —$C(CH_3)_2$—, —$C(CH_2CH_2)$—(cyclopropano), CO, —(CO)$CH_2$—, —$CH_2CH_2$—, or —CHCH—; U is a covalent bond, $CH_2$, —$CH(CH_3)$—, —$C(CH_3)_2$—, or —$CH_2CH_2$—; $R_1$ is an optionally substituted alkyl group, an optionally substituted 3-7 membered cycloalkyl or heterocyclyl group, an optionally substituted 6-membered aryl group, an optionally substituted 5- or 6-membered heteroaryl group, an optionally substituted 5,6- or 6,6-bicyclic heteroaryl group, or an optionally substituted bicyclic aryl group; $R_2$ is hydrogen, an optionally substituted 3-7 membered cycloalkyl or heterocyclyl group, an optionally substituted 6-membered aryl group, an optionally substituted 5- or 6-membered heteroaryl group, or an optionally substituted 5,6- or 6,6-bicyclic heteroaryl group, or an optionally substituted aryl group; $R_3$ is a halogen, or an optionally substituted alkyl or alkoxy group. In one embodiment, $R_2$ is a non-hydrogen substituent.

In a preferred embodiment, $R_1$ is an optionally substituted cycloalkyl or heterocyclyl group. Examples of specific preferred cycloalkyl and heterocyclyl groups are shown below wherein $R_{11}$ is the attachment point to the core scaffold. $R_{12}$ and $R_{13}$ are independently H, $CH_3$, $CF_3$, or F.

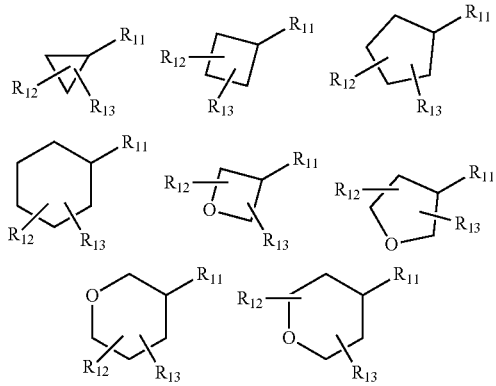

In another preferred embodiment, $R_1$ is an optionally substituted aryl or heteroaryl group. Examples of specific preferred aryl and heteroaryl groups are shown below wherein $R_{11}$ is the attachment point to the core scaffold, $R_{15}$ is H, halogen, alkyl, $CF_3$, $OCH_3$, $OCF_3$, or CN, and $R_{16}$ is H, halogen, alkyl, $CF_3$, $OCH_3$, $OCF_3$, CN, $NHCOR_{14}$, or $N(CH_3)COR_{14}$ wherein $R_{14}$ is alkyl, cycloalkyl, aryl or heteroaryl.

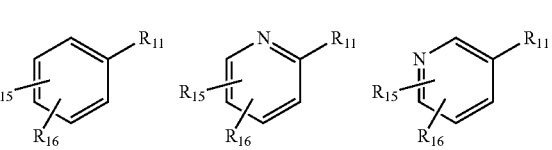

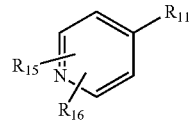

In another preferred embodiment, $R_1$ is an optionally substituted fused bicyclic group. Examples of specific preferred fused bicyclic groups are shown below wherein $R_{11}$ is the attachment point to the core scaffold, and $R_{15}$ and $R_{17}$ are independently H, halogen, alkyl, $CF_3$, $OCH_3$, $OCF_3$, or CN.

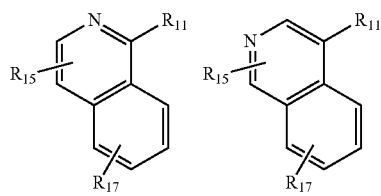

In another preferred embodiment, U is a covalent bond or $CH_2$, and $R_2$ is an optionally substituted 5 or 6-membered aryl or heteroaryl group, wherein $R_{18}$ is the attachment point to U, and $R_{15}$ and $R_{17}$ are independently H, halogen, alkyl, $CF_3$, $OCH_3$, $OCF_3$, or CN.

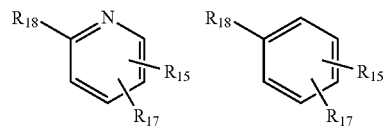

In another aspect, a compound provided herein is selected from:

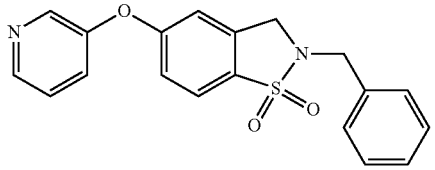

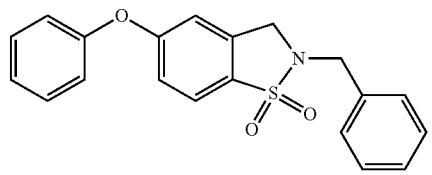

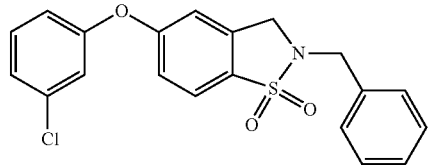

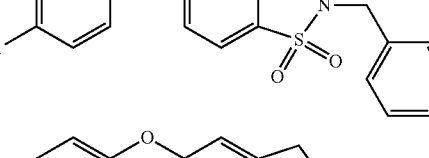

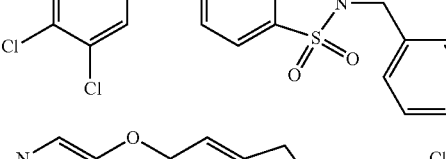

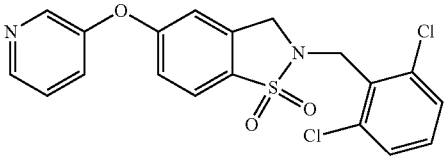

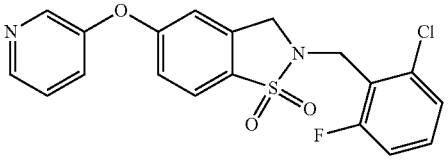

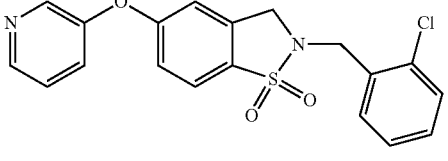

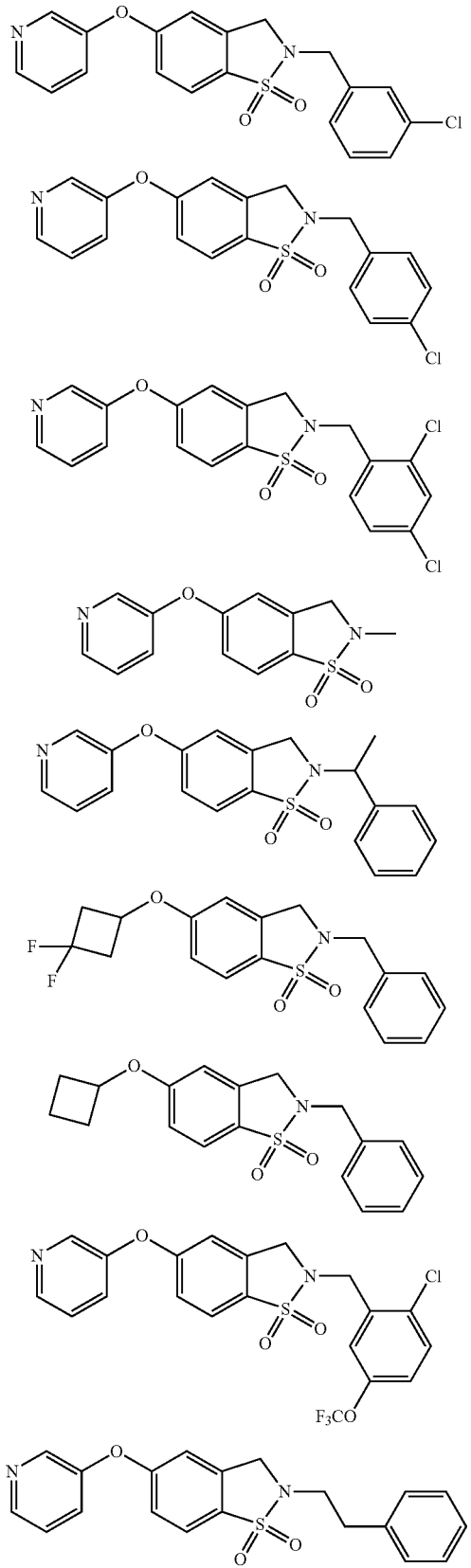
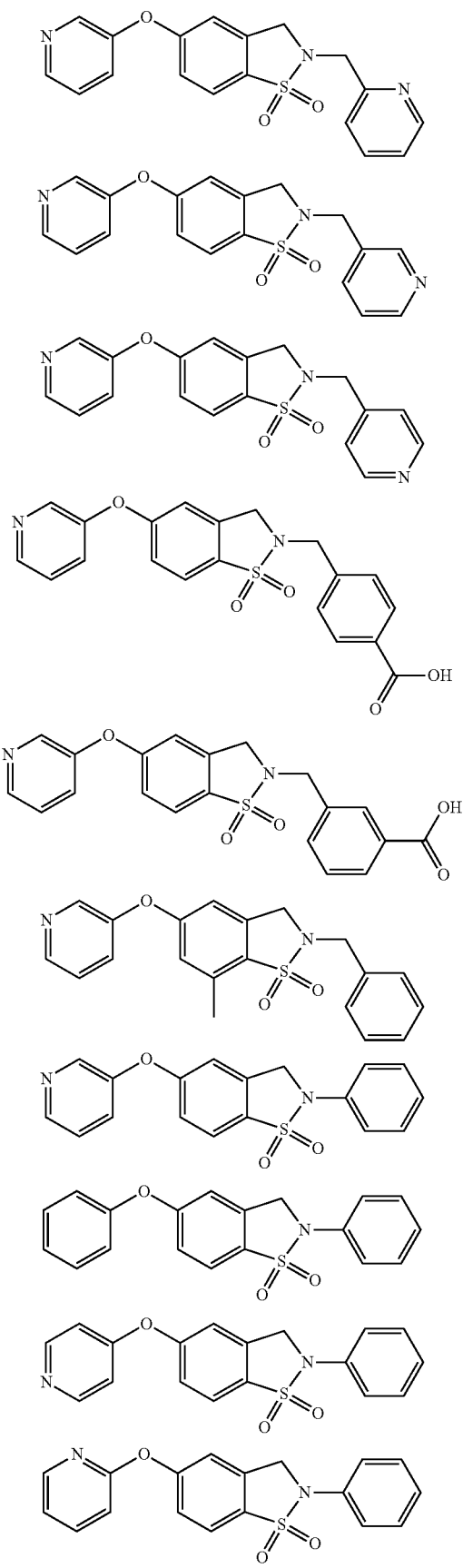

-continued

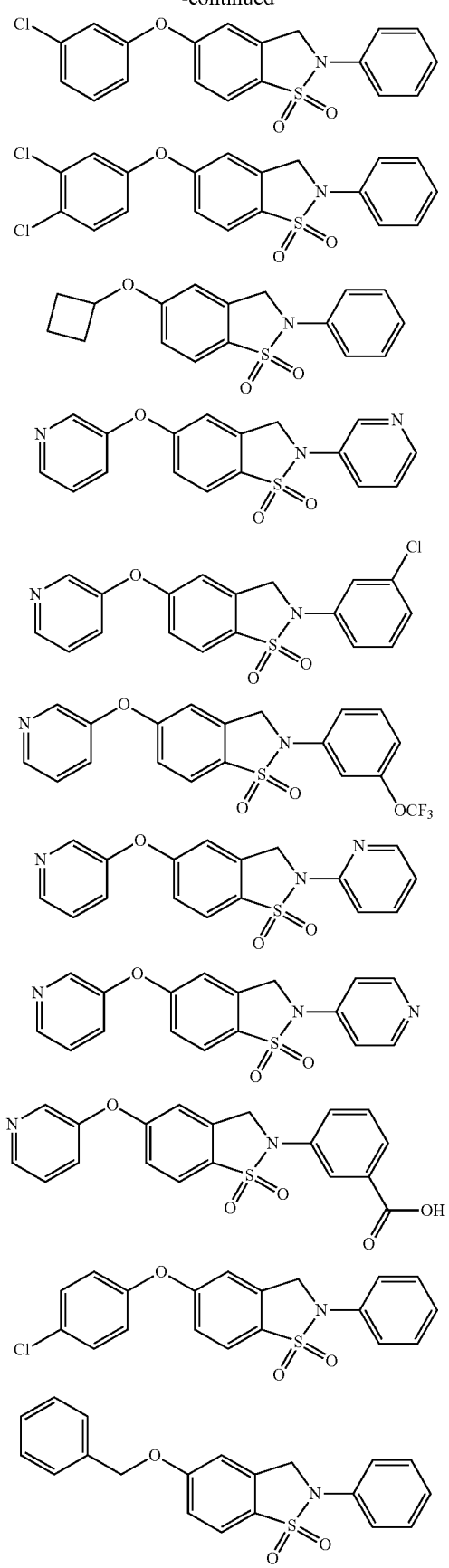

-continued

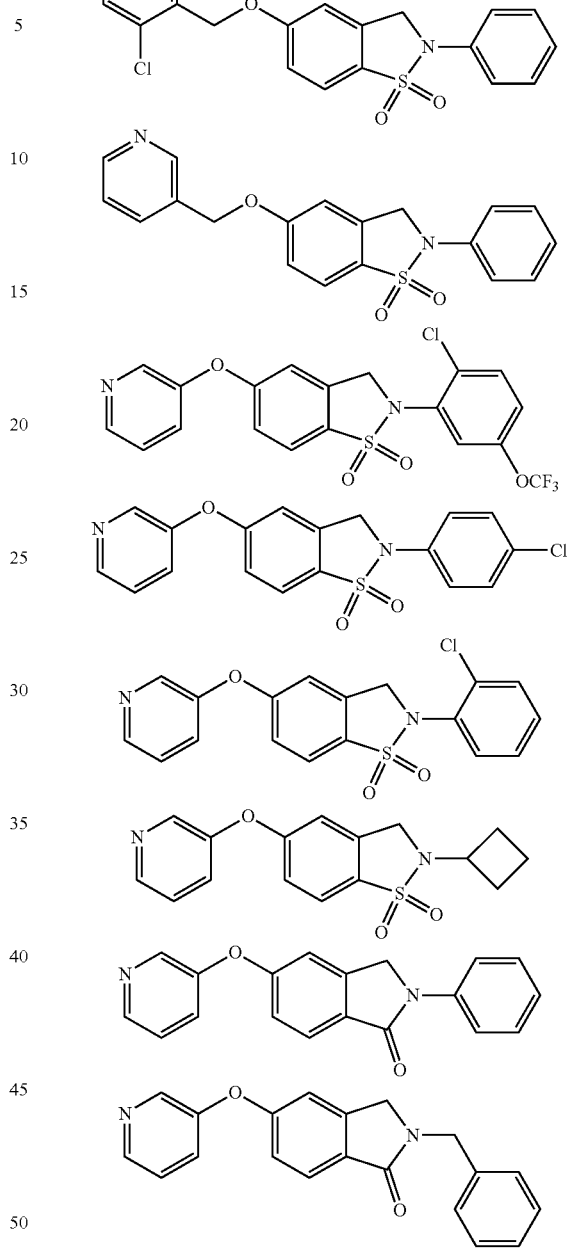

Certain compounds of the present invention are synthesized as schematically described herein below. Other compounds of the present invention can be synthesized by adapting these and other methods exemplified in the Examples section below or methods known to one of skill in the art upon appropriate substitution of starting materials, other reagents, and/or process conditions (i.e., reaction temperatures, times, mole ratios of reactants, solvents, pressures, and the like).

For compounds of the invention that contain one or more chiral centers, such compounds can be prepared or isolated as pure stereoisomers, i.e., as individual enantiomers or diastereomers, or as stereoisomer-enriched mixtures. All such stereoisomers (and enriched mixtures) are included within the scope of the compounds provided and utilized herein unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

In another aspect, the present invention provides compositions comprising a compound of the present invention, and at least one pharmaceutically acceptable excipient, i.e., pharmaceutical formulations. In general, the compounds of the present invention can be formulated for administration to a patient by any of the accepted modes of administration. Thus, the invention provides solid and liquid formulations of the compounds of the invention. Various formulations and drug delivery systems are available in the art. See, e.g., Gennaro, A. R., ed. (1995) *Remington's Pharmaceutical Sciences*, 18$^{th}$ ed., Mack Publishing Co.

Typically, compounds of the present invention will be administered as pharmaceutical compositions by one of the following routes: oral, systemic (e.g., transdermal, intranasal or by suppository), or parenteral (e.g., intramuscular, intravenous or subcutaneous) administration. Compositions can take the form of tablets, pills, capsules, semisolids, powders, sustained release formulations, solutions, suspensions, elixirs, aerosols, or any other appropriate compositions.

Pharmaceutical dosage forms of a compound of the present invention may be manufactured by any of the methods well-known in the art, such as, for example, by conventional mixing, sieving, dissolving, melting, granulating, dragee-making, tabletting, suspending, extruding, spray-drying, levigating, emulsifying, (nano/micro-) encapsulating, entrapping, or lyophilization processes. As noted above, the compositions of the present invention can include one or more physiologically acceptable inactive ingredients that facilitate processing of active molecules into preparations for pharmaceutical use.

Pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability. In some embodiments, the compounds of the present invention are formulated accordingly.

The compositions are comprised of in general, a compound of the present invention in combination with at least one pharmaceutically acceptable excipient. Acceptable excipients are non-toxic, aid administration, and do not adversely affect the therapeutic benefit of the claimed compounds. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols. Other suitable pharmaceutical excipients and their formulations are described in Remington's Pharmaceutical Sciences, edited by E. W. Martin (Mack Publishing Company, 18th ed., 1990).

The present compositions may, if desired, be presented in a pack or dispenser device containing one or more unit dosage forms containing the active ingredient. Such a pack or device may, for example, comprise metal or plastic foil, such as a blister pack, or glass, and rubber stoppers such as in vials. The pack or dispenser device may be accompanied by instructions for administration. Compositions comprising a compound of the invention formulated in a compatible pharmaceutical carrier may also be prepared, placed in an appropriate container, and labeled for treatment of an indicated condition.

The amount of the compound in a formulation can vary within the full range employed by those skilled in the art. Typically, the formulation will contain, on a weight percent (wt %) basis, from about 0.01-99.99 wt % of a compound of the present invention based on the total formulation, with the balance being one or more suitable pharmaceutical excipients. Generally, the compound is present at a level of about 1-80 wt %.

In another aspect, the invention provides a method of producing a therapeutic effect of GPR120 by contacting a therapeutically effective amount of a compound or a composition of the present invention with the GPR120 in need thereof. In one embodiment, the therapeutic effect is produced in a cell. In another embodiment, the contacting is performed in vitro or in vivo.

In another aspect, provided herein is a method of treating Type 2 diabetes in a subject in need thereof comprising administering to the subject a therapeutically effective amount of a compound or a composition of the present invention. In one embodiment, the subject is a human.

All technical and patent publications cited herein are incorporated herein by reference in their entirety.

The invention having been described in summary and in detail is illustrated and not limited by the examples below. Examples 1-46 illustrate specific compounds of the invention and methods for their synthesis. Examples 47 and 48 illustrate methods whereby the ability of compounds of the invention to activate the GPR120 receptor can be measured in biological assays.

SYNTHESIS EXAMPLES

Example 1

Synthesis of Compound 1

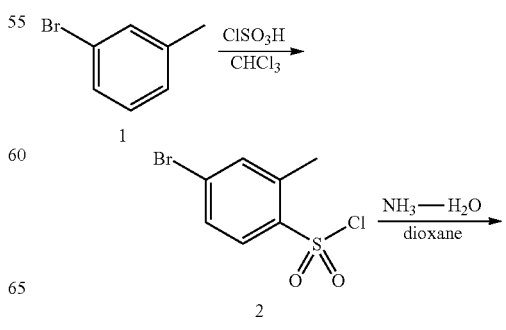

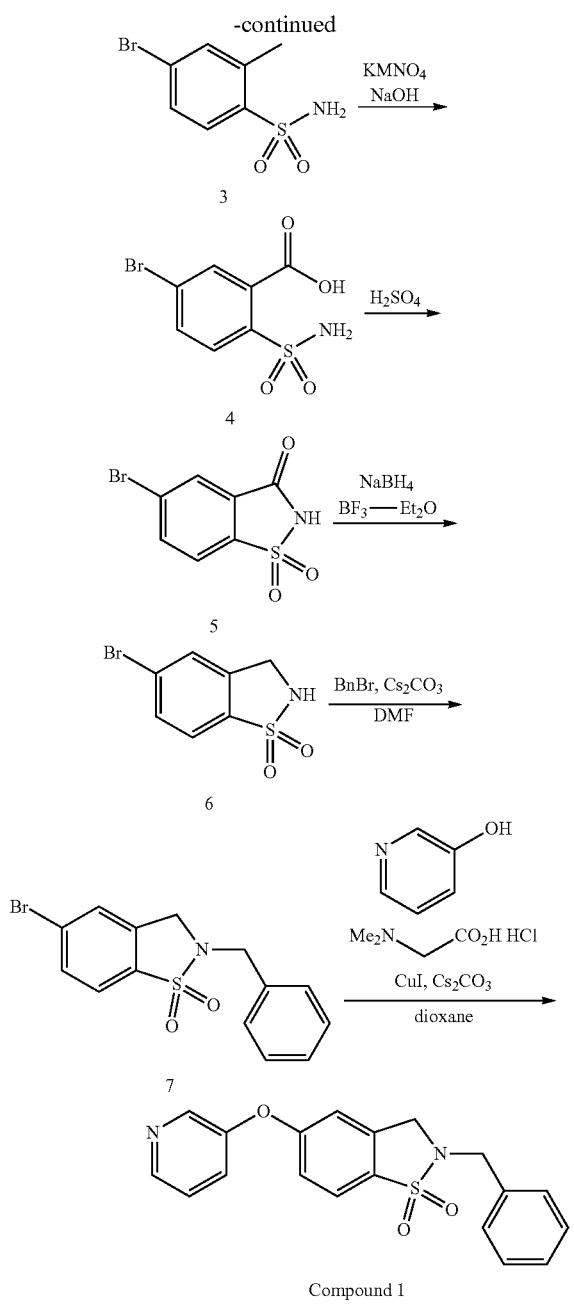

Step 1.

To a solution of 1 (50.0 g, 292 mmol) stirred in CHCl$_3$ (500 mL) was added chlorosulfuric acid (238 g, 2.05 mol) at 0° C. The reaction mixture was stirred at 0° C. for 0.5 h. When TLC showed the reaction was complete, the reaction mixture was poured into ice water (500 mL), extracted by CH$_2$Cl$_2$ (3×500 mL), dried over anhydrous Na$_2$SO$_4$, and concentrated. The crude material was washed with petroleum ether (20 mL) to afford 2 (49.2 g, 59%).

Step 2.

To a solution of 2 (40.0 g, 148 mmol) stirred in dioxane (800 mL) was added NH$_3$·H$_2$O (1.5 L, 15.58 mol) at 0° C. The reaction mixture was stirred at 0° C. for 1 h. When TLC showed the reaction was complete, the reaction mixture was extracted with CH$_2$Cl$_2$ (6×500 mL), dried over anhydrous Na$_2$SO$_4$, and concentrated. The crude material was washed with petroleum ether (100 mL) to afford 3 (36 g, 92% yield).

Step 3.

To a solution of NaOH (24.0 g, 600 mmol) in H$_2$O (240 mL) at 0° C. was added 3 (30.0 g, 120 mmol) and KMnO$_4$ (94.8 g, 600 mmol) portionwise. The reaction mixture was stirred at 60° C. for 12 h under N$_2$. When LCMS showed the reaction was complete, the reaction mixture was quenched by Na$_2$SO$_3$ (30 g) at 0° C. and filtered. The filtrate was acidified to pH=2 and filtered to afford 4 (25.0 g) as a solid which was used without further purification.

Step 4.

To concentrated H$_2$SO$_4$ (100 mL) was added 4 (10.0 g, 35.7 mmol) at 0° C. and the reaction mixture was stirred at 40° C. for 12 h. When LCMS showed the reaction was complete, the reaction mixture was poured into ice water (200 mL) and then extracted by ethyl acetate (3×200 mL). The organic layer was washed with H$_2$O (3×20 mL), dried over anhydrous Na$_2$SO$_4$, and concentrated to afford 5 (9.1 g).

Step 5.

To a solution of 5 (9.1 g, 34.7 mmol) stirred in THF (200 mL) was added NaBH$_4$ (13.1 g, 347 mmol) and BF$_3$.Et$_2$O (49.3 g, 347 mmol) portionwise at 0° C. The reaction mixture was stirred at 70° C. for 12 h under N$_2$. When LCMS showed the reaction was complete, the reaction mixture was poured into ice water (250 mL) and extracted with ethyl acetate (3×200 mL). The organic layer was washed with H$_2$O (100 mL), dried over anhydrous Na$_2$SO$_4$, and concentrated to afford 6 (8.6 g).

Step 6.

To a solution of 6 (50 mg, 0.20 mmol) and benzyl bromide (52 mg, 0.30 mmol) in DMF (2 mL) was added cesium carbonate (197 mg, 0.60 mmol). The reaction mixture was stirred 12 h at room temperature under an inert atmosphere. Upon completion, the reaction mixture was concentrated under reduced pressure and purified by prep-TLC to afford 7 (30 mg).

Step 7.

To a solution of 7 (31 mg, 0.092 mmol) and pyridin-3-ol (8.8 mg, 0.092 mmol) in dioxane (2 mL) was added cesium carbonate (90 mg, 0.028 mmol), CuI (7 mg, 0.037 mmol), and 2-(dimethylamino)acetic acid hydrochloride (2.6 mg, 0.018 mmol). The reaction mixture was stirred at 90° C. under inert atmosphere for 12 h. Upon completion, the reaction was concentrated and purified by prep-HPLC (0.04% HCl/CH$_3$CN/H$_2$O system) to afford Compound 1 (10 mg, 31%) as a white solid. $^1$H NMR (CD$_3$OD, 400 MHz) δ 8.26-8.24 (d, 1H), 8.07-7.95 (s, 1H), 7.96-7.93 (d, 1H), 7.45-7.32 (m, 2H), 4.43 (s, 2H), 4.28 (s, 2H); LCMS (ESI): m/z 353.0 (M+H).

Example 2

Synthesis of Compound 2

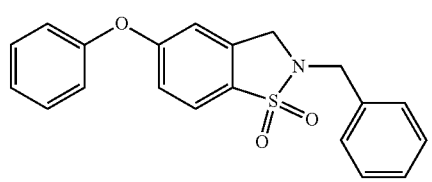 [SMILES: O=S1(=O)c2ccc(Oc3ccccc3)cc2CN1Cc1ccccc1]

Compound 2 was prepared in a manner similar to Compound 1. $^1$H NMR (DMSO-d$_6$, 400 MHz) δ 7.91-7.89 (d, 1H), 7.45-7.38 (m, 7H), 7.25-7.23 (m, 1H), 7.14-7.10 (m, 4H), 4.36 (s, 2H), 4.24 (s, 2H); LCMS (ESI): m/z 352.0 (M+H).

Example 3

Synthesis of Compound 3

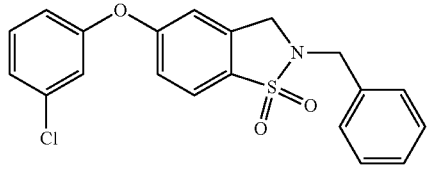 [SMILES: O=S1(=O)c2ccc(Oc3cccc(Cl)c3)cc2CN1Cc1ccccc1]

Example 3 was prepared in a manner similar to Compound 1. ¹H NMR (DMSO-d$_6$, 400 MHz) δ 7.82-7.80 (d, 1H), 7.44-7.43 (d, 2H), 7.39-7.35 (m, 4H), 7.21-7.20 (m, 2H), 7.13-7.12 (d, 1H), 7.04-7.02 (m, 2H), 4.40 (s, 2H), 4.21 (s, 2H); LCMS (ESI): m/z 386.0 (M+H).

Example 4

Synthesis of Compound 4

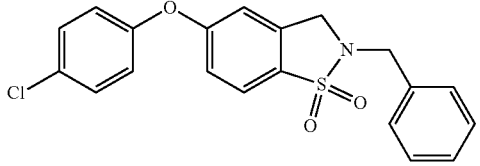 [SMILES: O=S1(=O)c2ccc(Oc3ccc(Cl)cc3)cc2CN1Cc1ccccc1]

Compound 4 was prepared in a manner similar to Compound 1. ¹H NMR (DMSO-d$_6$, 400 MHz) δ 7.80-7.78 (d, 1H), 7.44-7.31 (m, 7H), 7.19-7.18 (d, 1H), 7.08-7.06 (d, 2H), 7.01 (s, 1H), 4.39 (s, 2H), 4.20 (s, 2H); LCMS (ESI): m/z 386.0 (M+H).

Example 5

Synthesis of Compound 5

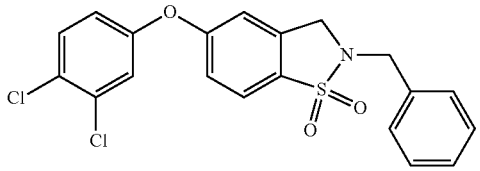 [SMILES: O=S1(=O)c2ccc(Oc3ccc(Cl)c(Cl)c3)cc2CN1Cc1ccccc1]

Compound 5 was prepared in a manner similar to Compound 1. ¹H NMR (DMSO-d$_6$, 400 MHz) δ 7.94-7.92 (d, 1H), 7.69-7.67 (d, 1H), 7.51-7.50 (d, 1H), 7.42-7.40 (m, 5H), 7.39-7.37 (d, 1H), 7.27 (s, 1H), 7.20-7.16 (d, 1H), 4.37 (s, 2H), 4.24 (s, 2H); LCMS (ESI): m/z 420.0 (M+H).

Example 6

Synthesis of Compound 6

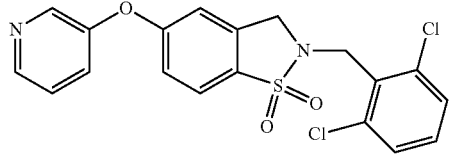 [SMILES: O=S1(=O)c2ccc(Oc3cccnc3)cc2CN1Cc1c(Cl)cccc1Cl]

Compound 6 was prepared in a manner similar to Compound 1. ¹H NMR (DMSO-d$_6$, 400 MHz) δ 7.93-7.90 (d, 1H), 7.68-7.66 (d, 1H), 7.56-7.54 (m, 3H), 7.45-7.43 (m, 2H), 7.39-7.26 (m, 1H), 4.58 (s, 2H), 4.32 (s, 2H); LCMS (ESI): m/z 421.0 (M+H).

Example 7

Synthesis of Compound 7

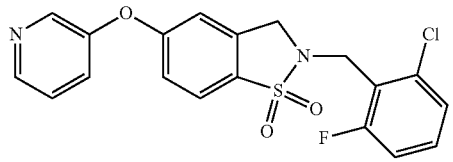 [SMILES: O=S1(=O)c2ccc(Oc3cccnc3)cc2CN1Cc1c(F)cccc1Cl]

Compound 7 was prepared in a manner similar to Compound 1. ¹H NMR (CD$_3$OD, 400 MHz) δ 8.79-8.68 (d, 1H), 8.28-8.26 (d, 1H), 8.06-8.04 (m, 1H), 7.92-7.90 (d, 1H), 7.43-7.32 (m, 4H), 7.20-7.15 (m, 1H), 4.61 (s, 2H), 4.42 (s, 2H); LCMS (ESI): m/z 405.0 (M+H).

Example 8

Synthesis of Compound 8

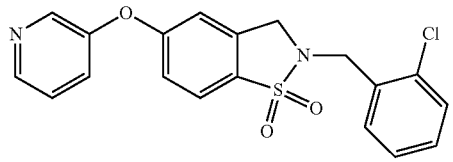 [SMILES: O=S1(=O)c2ccc(Oc3cccnc3)cc2CN1Cc1ccccc1Cl]

Compound 8 was prepared in a manner similar to Compound 1. ¹H NMR (DMSO-d$_6$ 400 MHz) δ 8.52-8.48 (t, 2H), 7.95-7.67 (m, 1H), 7.53-7.51 (m, 1H), 7.39-7.28 (m, 1H), 7.28-7.20 (m, 1H), 4.48 (s, 2H), 4.37 (s, 2H); LCMS (ESI): m/z 387.0 (M+H).

Example 9

Synthesis of Compound 9

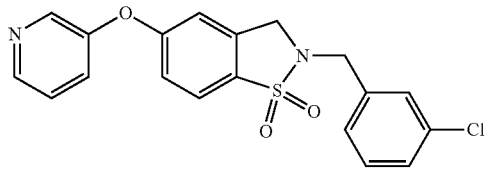 [SMILES: O=S1(=O)c2ccc(Oc3cccnc3)cc2CN1Cc1cccc(Cl)c1]

Compound 9 was prepared in a manner similar to Compound 1. $^1$H NMR (CD$_3$OD, 400 MHz) δ 8.81-8.69 (d, 2H), 8.31-8.29 (d, 1H), 8.10-8.08 (m, 1H), 7.97-7.95 (d, 1H), 7.49-7.44 (m, 2H), 7.39-7.33 (m, 4H), 4.45 (s, 2H), 4.33 (s, 2H); LCMS (ESI): m/z 387.0 (M+H).

Example 10

Synthesis of Compound 10

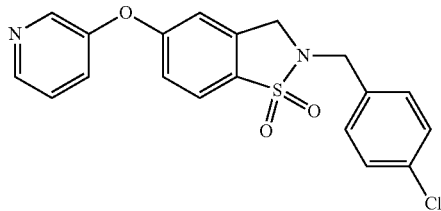 [SMILES: O=S1(=O)c2ccc(Oc3cccnc3)cc2CN1Cc1ccc(Cl)cc1]

Compound 10 was prepared in a manner similar to Compound 1. $^1$H NMR (CD$_3$OD, 400 MHz) δ 8.82 (s, 1H), 8.70 (s, 1H), 8.34-8.32 (d, 1H), 8.11-8.08 (m, 1H), 7.96-7.94 (d, 1H), 7.46-7.36 (m, 6H), 4.43 (s, 2H), 4.31 (s, 2H); LCMS (ESI): m/z 387.0 (M+H).

Example 11

Synthesis of Compound 11

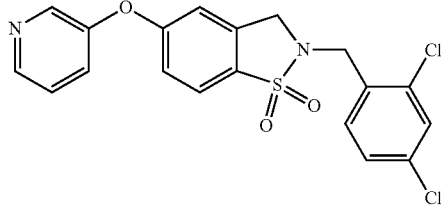 [SMILES: O=S1(=O)c2ccc(Oc3cccnc3)cc2CN1Cc1ccc(Cl)cc1Cl]

Compound 11 was prepared in a manner similar to Compound 1. $^1$H NMR (CD$_3$OD, 400 MHz) δ 8.55-8.49 (m, 2H), 7.95 (d, 1H), 7.69 (bs, 2H), 7.60-7.53 (m, 2H), 7.51-7.47 (m, 1H), 7.28 (d, 1H), 7.20 (s, 1H), 4.47 (s, 2H), 4.38 (s, 2H); LCMS (ESI): m/z 421.0 (M+H).

Example 12

Synthesis of Compound 12

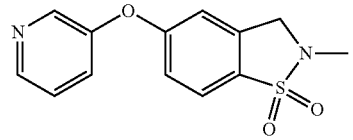 [SMILES: CN1Cc2cc(Oc3cccnc3)ccc2S1(=O)=O]

Compound 12 was prepared in a manner similar to Compound 1. $^1$H NMR (CD$_3$OD, 400 MHz) δ 8.82 (s, 1H), 8.70-8.68 (d, 1H), 8.36-8.33 (d, 1H), 8.12-8.10 (d, 1H), 7.44-7.40 (m, 2H), 4.40 (s, 2H), 2.90 (s, 3H); LCMS (ESI): m/z 277.0 (M+H).

Example 13

Synthesis of Compound 13

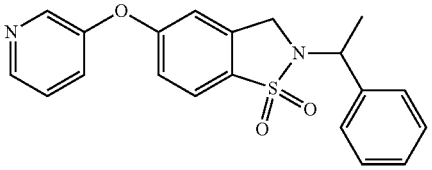 [SMILES: CC(c1ccccc1)N1Cc2cc(Oc3cccnc3)ccc2S1(=O)=O]

Compound 13 was prepared in a manner similar to Compound 1. $^1$H NMR (CD$_3$OD, 400 MHz) δ 8.78 (d, 2H), 8.27-8.25 (d, 2H), 7.92-7.90 (d, 1H), 7.49-7.47 (d, 1H), 7.38-7.29 (m, 8H), 4.96-4.93 (m, 1H), 4.36-4.32 (d, 1H), 4.06-4.02 (d, 1H), 1.79-1.77 (d, 3H); LCMS (ESI): m/z 367.0 (M+H).

Example 14

Synthesis of Compound 14

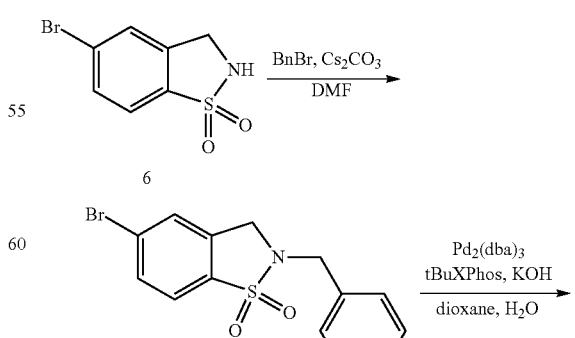

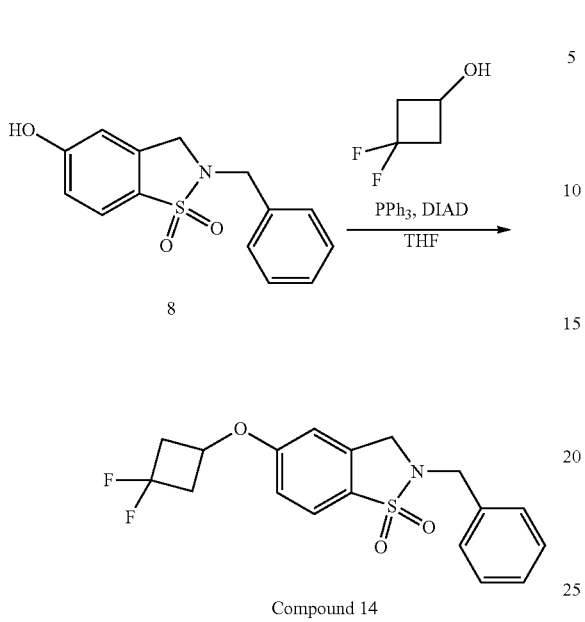

8

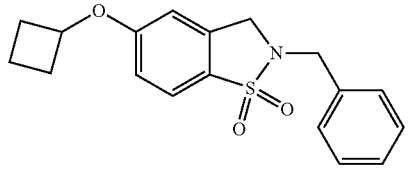 [SMILES: O=S1(=O)c2ccc(OC3CCC3)cc2CN1Cc1ccccc1]

Compound 14

Step 1.

To a solution of 6 (1.0 g, 4.03 mmol) in DMF (15 mL) was added $Cs_2CO_3$ (2.63 g, 8.06 mmol) and benzyl bromide (1.03 g, 6.05 mmol). The mixture was stirred at 30° C. for 12 hours and then filtered. The filtrate was concentrated under reduced pressure to give a residue, which was diluted with water (80 mL) and extracted with $CH_2Cl_2$ (3×60 mL). The combined organic layers were washed with water (3×60 mL) and brine (2×80 mL), dried over anhydrous $Na_2SO_4$, filtered, and concentrated under reduced pressure to afford 7 (1.2 g) as a white solid which was used directly in the next step without purification.

Step 2.

A mixture of 7 (120 mg crude material), $Pd_2(dba)_3$ (65 mg, 0.071 mmol), t-Bu Xphos (30 mg, 0.071 mmol) and KOH (99.5 mg, 1.77 mmol) in dioxane (2 mL) and $H_2O$ (2 mL) was degassed, purged with $N_2$ (3×), and then stirred at 85° C. for 12 hours. The reaction mixture was concentrated under reduced pressure to give a residue that was diluted with water (5 mL). The solution was adjusted to pH=3 using 2M HCl and then extracted with ethyl acetate (3×15 mL). The organic layer was washed with brine (2×20 mL), dried over anhydrous $Na_2SO_4$, filtered and concentrated under reduced pressure to give 8 (130 mg) as a yellow solid which was used directly in the next step without purification.

Step 3.

A solution of 8 (50 mg, 0.18 mmol), 3,3-difluorocyclobutanol (23.6 mg, 0.22 mmol), $PPh_3$ (95 mg, 0.36 mmol) and DIAD (74 mg, 0.36 mmol) was stirred in THF (2 mL) at 35° C. under $N_2$ for 12 hours. When LCMS showed the reaction was complete, the reaction mixture was concentrated to give a residue. The residue was purified by prep-HPLC (0.04% HCl/ACN/$H_2O$ system) to give Compound 14 (14 mg, 21%) as a white solid. $^1$H NMR ($CD_3OD$, 400 MHz) δ 7.74-7.46 (d, 1H), 7.44-7.38 (d, 2H), 7.36-7.32 (m, 2H), 7.11-7.09 (d, 1H), 6.93 (s, 1H), 4.80 (s, 2H), 4.21 (s, 2H), 3.31-3.12 (m, 2H), 2.76-2.69 (m, 2H); LCMS (ESI): m/z 366.0 (M+H).

Example 15

Synthesis of Compound 15

Compound 15 was prepared in a manner similar to Compound 14. $^1$H NMR (DMSO-$d_6$, 400 MHz) δ 7.79-7.76 (d, 1H), 7.43-7.37 (m, 4H), 7.34-7.33 (m, 1H), 7.04-7.02 (m, 1H), 6.98 (s, 1H), 4.77-4.70 (m, 1H), 4.34 (s, 2H), 4.21 (s, 2H), 2.50-2.43 (m, 2H), 2.05-2.00 (m, 2H), 1.79-1.77 (m, 1H), 1.61-1.64 (m, 1H); LCMS (ESI): m/z 330.1 (M+H).

Example 16

Synthesis of Compound 16

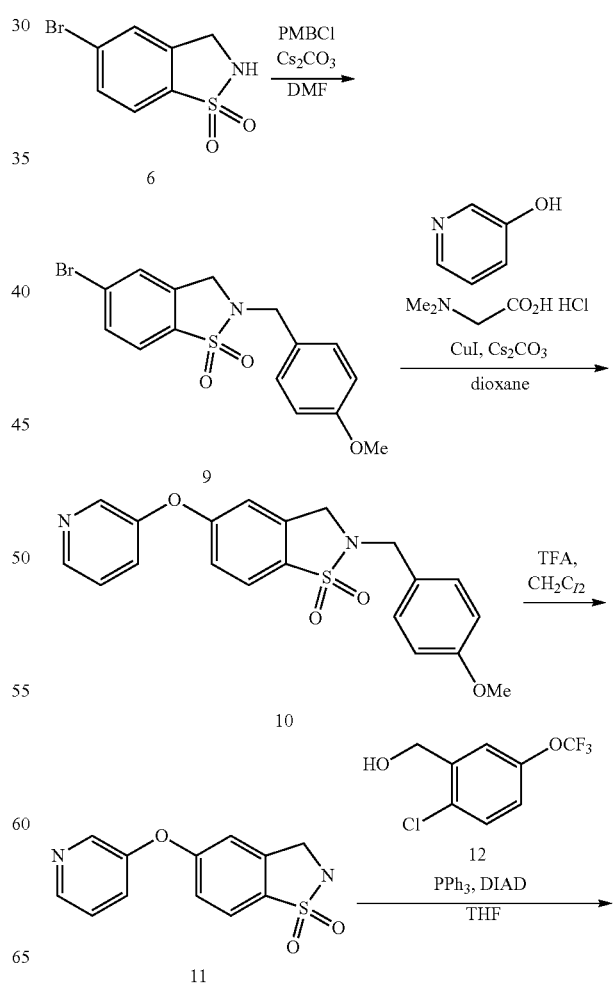

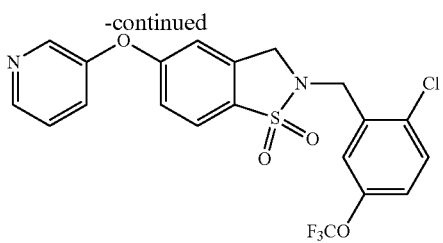

Compound 16

Step 1.

To a solution of 6 (300 mg, 1.21 mmol) and PMBCl (284 mg, 1.81 mmol) stirred in DMF (2. mL) was added $Cs_2CO_3$ (788 mg, 2.42 mmol). The reaction mixture was stirred at 35° C. for 12 h. When LCMS showed the reaction was complete, the reaction mixture was quenched by $H_2O$ (10 mL) and extracted with ethyl acetate (3×20 mL). The organic layer was washed with $H_2O$ (3×20 mL), dried over anhydrous $Na_2SO_4$, concentrated, and purified by prep-TLC (petroleum ether:ethyl acetate=1:1) to afford 9 (335 mg, 64%).

Step 2.

To a solution of 9 (1.50 g, 4.07 mmol) and pyridin-3-ol (775 mg, 8.15 mmol) stirred in dioxane (15 mL) was added CuI (620 mg, 3.26 mmol), $Cs_2CO_3$ (3.32 g, 10.2 mmol) and 2-(dimethylamino)acetic acid hydrochloride (227 mg, 1.63 mmol). The reaction mixture was stirred at 100° C. under $N_2$ for 12 h. When LCMS showed the reaction was complete, the reaction mixture was filtered. The filtrate was concentrated and purified by prep-TLC (petroleum ether:ethyl acetate=1:1.5) to afford 10 (770 mg, 42%) as a liquid.

Step 3.

A solution of 10 (770 mg, 2.01 mmol) stirred in TFA/ $CH_2Cl_2$ (77 mL) at 25° C. 12 h. When LCMS showed that the reaction was complete, the reaction mixture was concentrated. The crude material was dissolved in methyl-t-butylether (15 mL) and $H_2O$ (10 mL). The water layer was adjusted to pH=10 and concentrated. The solid was washed by $CH_2Cl_2$: MeOH=10:1 (30 mL) to produce 11 (500 mg, 76%) as a solid. LCMS (ESI): m/z 263.1. (M+H).

Step 4.

To a solution of 11 (80 mg, 0.31 mmol), 12 (69 mg, 31 mmol) and $PPh_3$ (80 mg, 0.31 mmol) stirred in THF (2 mL) was added DIAD (62 mg, 0.31 mmol). The reaction mixture was stirred at 40° C. under $N_2$ for 12 h. When LCMS showed the reaction was complete, the reaction mixture was concentrated. The crude material was purified by prep-HPLC to afford Compound 16 (8.7 mg, 6%). $^1$H NMR ($CD_3OD$ 400 MHz) δ 8.443 (s, 2H), 7.87-7.85 (d, 1H), 7.85-7.67 (d, 1H), 7.64-7.57 (m, 3H), 7.50-7.29 (d, 2H), 4.59 (s, 2H), 4.42 (s, 2H); LCMS (ESI): m/z 471.1 (M+H).

Example 17

Synthesis of Compound 17

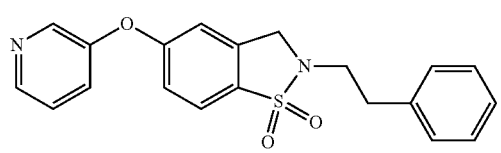 [SMILES: O=S1(=O)c2ccc(Oc3cccnc3)cc2CN1CCc1ccccc1]

Compound 17 was prepared in a manner similar to Compound 16. $^1$H NMR ($CD_3OD$, 400 MHz) δ 7.83-7.81 (d, 2H), 7.33-7.28 (s, 6H), 7.22-7.21 (m, 2H), 4.34 (d, 2H), 3.51-3.48 (m, 2H), 3.05-3.01 (s, 2H); LCMS (ESI): m/z 367.1 (M+H).

Example 18

Synthesis of Compound 18

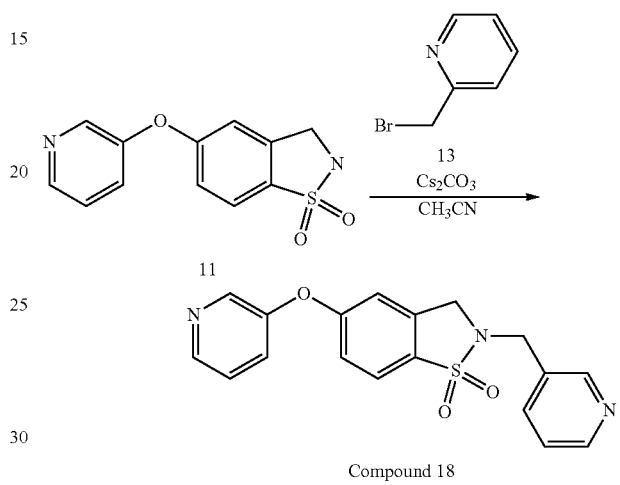

Compound 18

To a solution of 11 (80 mg, 0.18 mmol) in $CH_3CN$ (3 mL) was added $Cs_2CO_3$ (149 mg, 046 mmol) and 13 (38 mg, 0.22 mmol). The mixture was stirred at 20° C. for 2 hours and then filtered. The filtrate was concentrated under reduced pressure to give a residue which was purified by prep-HPLC (HCl, 0.05% HCl-ACN) to afford Compound 18 (24 mg, 36% yield) as a yellow oil. $^1$H NMR ($CD_3OD$, 400 MHz) δ 8.86-8.85 (d, 2H), 8.72-8.71 (d, 1H), 8.67-8.65 (m, 1H), 8.24-8.22 (d, 1H), 8.14-8.12 (m, 1H), 8.05-7.99 (m, 2H), 8.01-7.99 (d, 1H), 7.48-7.51 (m, 2H), 4.99 (s, 2H), 4.70 (s, 2H); LCMS (ESI): m/z 354.0 (M+H).

Example 19

Synthesis of Compound 19

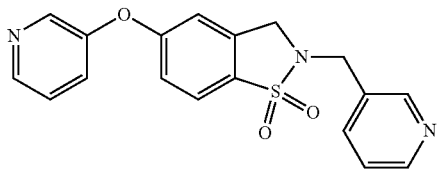 [SMILES: O=S1(=O)c2ccc(Oc3cccnc3)cc2CN1Cc1cccnc1]

Compound 19 was prepared in a manner similar to Compound 18. $^1$H NMR ($CD_3OD$, 400 MHz) δ 9.01 (s, 1H), 8.88-8.87 (d, 2H), 8.80-8.78 (d, 1H), 8.73-8.72 (d, 1H), 8.40-8.38 (d, 1H), 8.18-8.12 (m, 2H), 7.99-7.97 (d, 1H), 7.51-7.46 (m, 2H), 4.81 (s, 2H), 4.59 (s, 2H); LCMS (ESI): m/z 354.0 (M+H).

Example 20

Synthesis of Compound 20

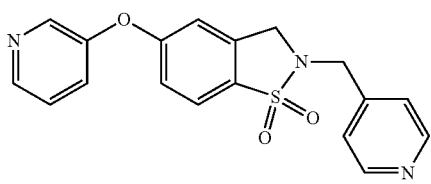 [SMILES: O=S1(=O)c2ccc(Oc3cccnc3)cc2CN1Cc1ccncc1]

Compound 20 was prepared in a manner similar to Compound 18. $^1$H NMR (CD$_3$OD, 400 MHz) δ 8.88-8.87 (m, 3H), 8.72-8.71 (d, 1H), 8.40-8.38 (d, 1H), 8.22-8.21 (d, 2H), 8.15-8.11 (m, 1H), 8.01-7.99 (d, 1H), 7.51-7.47 (m, 2H), 4.90 (s, 2H), 4.62 (s, 2H); LCMS (ESI): m/z 354.0 (M+H).

Example 21

Synthesis of Compound 21

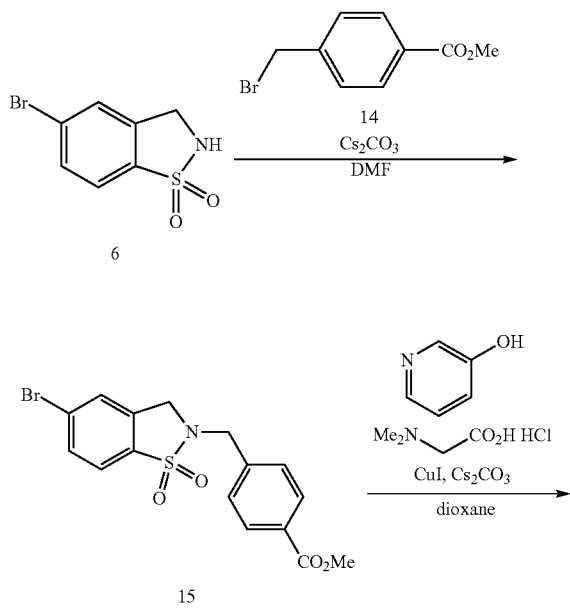

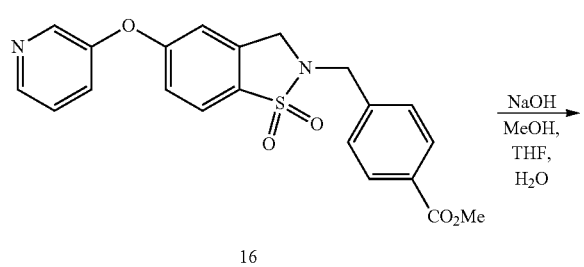

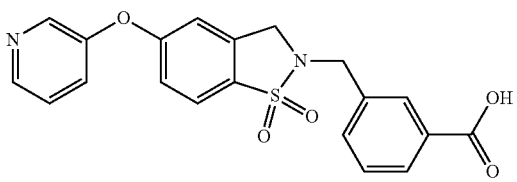 [SMILES: O=C(O)c1cccc(CN2Cc3cc(Oc4cccnc4)ccc3S2(=O)=O)c1]

Compound 21

Step 1.

A mixture of 6 (150 mg, 0.60 mmol), 14 (180 mg, 0.79 mmol), Cs$_2$CO$_3$ (393 mg, 1.21 mmol) in DMF (2 mL) was degassed, purged with N$_2$ (3×), and then stirred at 35° C. for 12 h. When the reaction was complete by LC-MS, it was filtered and diluted with ethyl acetate (30 mL). The organic layer was washed with water (3×30 mL) and brine (30 mL), dried over anhydrous sodium sulfate, filtered, and concentrated. The crude material (180 mg, white solid) was used directly for next step without purification.

Step 2.

A mixture of 15 (180 mg, 0.27 mmol), pyridin-3-ol (33 mg, 0.35 mmol), CuI (15 mg, 0.08 mmol), Cs$_2$CO$_3$ (174 mg, 0.53 mmol) and 2-(dimethylamino)acetic acid hydrochloride (11 mg, 0.08 mmol) in dioxane (2 mL) was degassed, purged with N$_2$ (3×), and then stirred at 100° C. for 24 hours. The reaction mixture was cooled, diluted with water (20 mL), and extracted with ethyl acetate (3×10 mL). The combined organic layer was washed with brine (30 mL), dried over anhydrous sodium sulfate, filtered and concentrated. The crude material was purified by prep-TLC (petroleum ether:ethyl acetate=1:1) to provide 16 (80 mg, 0.15 mmol) as a light yellow oil.

Step 3.

To a solution of 16 (80 mg, 0.15 mmol) in THF (1 mL) and MeOH (1 mL) was added NaOH (1 mL, 2M). The mixture was stirred at 15° C. for 0.5 h, diluted with water (30 mL), and then acidified with 2N HCl (aq) to pH=6. The solution was extracted with ethyl acetate (3×10 mL); the organic layer was washed with brine (30 mL), dried over anhydrous sodium sulfate, filtered and concentrated. The crude material was purified by prep-HPLC to give Compound 21 (8.9 mg, 13%) as a white solid. $^1$H NMR (DMSO-d$_6$, 400 MHz) δ 8.54 (d, 2H), 7.99-7.93 (m, 3H), 7.73 (d, 1H), 7.61-7.50 (m, 3H), 7.29 (d, 1H), 7.21 (s, 1H), 4.47 (s, 2H), 4.30 (s, 2H).

Example 22

Synthesis of Compound 22

Compound 22 was prepared in a manner similar to Compound 21. $^1$H NMR (DMSO-d$_6$, 400 MHz) δ 8.58 (s, 2H), 8.02-7.94 (m, 2H), 7.90 (d, 1H), 7.78 (d, 1H), 7.70-7.60

(m, 2H), 7.56-7.48 (m, 1H), 7.30 (d, 1H), 7.22 (s, 1H), 4.47 (s, 2H), 4.28 (s, 2H); LCMS (ESI): m/z 397.0 (M+H).

Example 23

Synthesis of Compound 23

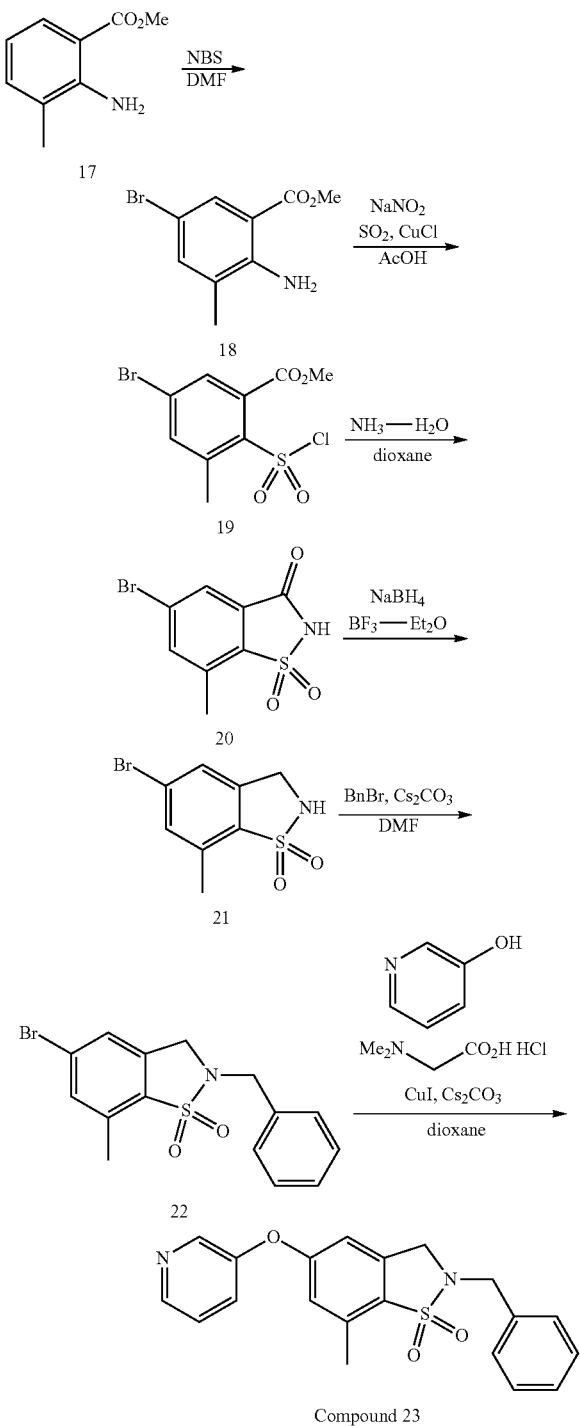

Step 1.

To a solution of 17 (15.0 g, 90.8 mmol) in DMF (200 mL) was added NBS (16.2 g, 90.8 mmol) at 0° C. After addition, the mixture was warmed to 15° C. and stirred for 14 hours. The reaction mixture was quenched by addition of water (200 mL) and then extracted with ethyl acetate (3×250 mL). The combined organic phase was washed with water (3×250 mL) and brine (2×200 mL), dried over anhydrous Na$_2$SO$_4$, filtered and concentrated in vacuo to give 18 (21.0 g) as a gray solid which was used directly in the next transformation. $^1$H NMR (CDCl$_3$, 400 MHz) δ 7.90-7.89 (d, 1H), 7.29-7.28 (d, 1H), 5.84 (s, 2H), 3.87 (s, 3H), 2.15 (s, 3H); LCMS (ESI): m/z 246.0 (M+H).

Step 2.

To a solution of 18 (11.0 g) in HCl (120 mL) and AcOH (20 mL) was added drop wise NaNO$_2$ (3.42 g, 49.6 mmol) in H$_2$O (20 mL) at 0° C. The mixture was stirred at 0° C. for 30 minutes and then SO$_2$ (17.3 g, 270 mmol) and CuCl (1.34 g, 13.5 mmol) in AcOH (200 mL) was added portion wise. After 30 minutes at 0° C., the reaction mixture was poured into water (300 mL) and extracted with CH$_2$Cl$_2$ (3×300 mL). The organic layer was washed with saturated brine (2×300 mL), dried over anhydrous Na$_2$SO$_4$, filtered and concentrated under reduced pressure to give 19 (12.0 g) as a brown oil which was used without further purification.

Step 3.

To a solution of NH$_3$·H$_2$O (200 mL) in dioxane (100 mL) was added 19 (11.0 g, 33.6 mmol) in dioxane (100 mL) at 0° C. After 30 minutes at 15° C., the reaction mixture was diluted with water (100 mL) and then extracted with ethyl acetate (3×300 mL). The combined organic phase was washed with saturated brine (2×300 mL), dried over anhydrous Na$_2$SO$_4$, filtered and concentrated in vacuo to give a residue which was purified by re-crystallization from methyl-t-butylether (100 mL) to give 20 (1.0 g) as a white solid. LCMS (ESI): m/z 276.0 (M−H).

Step 4.

To a solution of 20 (200 mg, 0.72 mmol) in THF (10.0 mL) was added NaBH$_4$ (274 mg, 7.24 mmol) portion wise at 0° C. After addition, BF$_3$.Et$_2$O (1.03 g, 7.24 mmol) was added portion wise. The resulting mixture was stirred at 70° C. for 14 hours. The reaction mixture was quenched with water (40 mL) and then extracted with ethyl acetate (3×50 mL). The organic phase was washed with saturated brine (2×50 mL), dried over anhydrous Na$_2$SO$_4$, filtered and concentrated in vacuo to give 21 (160 mg, crude) as a white solid which was used without further purification. LCMS (ESI): m/z 262.0 (M−H).

Step 5.

To a solution of 21 (120 mg, crude) in DMF (6.0 mL) was added Cs$_2$CO$_3$ (298 mg, 0.92 mmol) and BnBr (117 mg, 0.69 mmol). The mixture was stirred at 30° C. for 14 hours. The reaction mixture was filtered and then diluted with water (20 mL) and extracted with ethyl acetate (3×20 mL). The organic layer was washed with water (3×15 mL) and saturated brine (2×20 mL), dried over anhydrous Na$_2$SO$_4$, filtered and concentrated under reduced pressure to give 22 (200 mg) as a yellow oil, which was used directly into the next step without further purification.

Step 6.

A mixture of 22 (140 mg), pyridine-3-ol (45 mg, 0.48 mmol), CuI (30 mg, 0.16 mmol), N,N-dimethylglycine hydrochloride (11 mg, 0.079 mmol) and Cs$_2$CO$_3$ (259 mg, 0.79 mmol) in dioxane (6.0 mL) was degassed and purged with N$_2$ (3×). The mixture was stirred at 100° C. for 14 hours and then filtered. The filtrate was concentrated under reduced pressure to give a residue, which was purified by prep-HPLC to afford Compound 23 (72 mg, 91%) as a colorless oil. $^1$H NMR (MeOD, 400 MHz) δ 8.79-8.78 (d, 1H), 8.68-8.67 (d, 1H), 8.33-8.31 (m, 1H), 8.11-8.09 (m, 1H), 7.46-7.44 (m, 2H), 7.39-7.32 (m, 3H), 7.26-7.25 (d, 1H), 7.15-7.14 (d, 1H), 4.44 (s, 2H), 4.24 (s, 2H), 2.63 (s, 3H); LCMS (ESI): m/z 486.2 (M+H).

Example 24

Synthesis of Compound 24

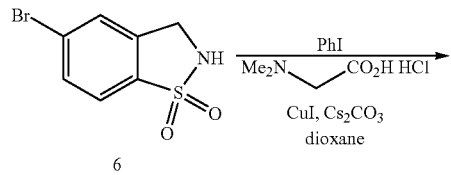

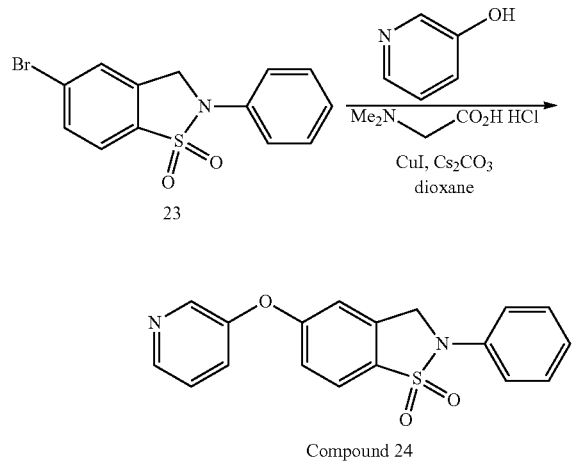

Step 1.

To a solution of 6 (1.00 g, 3.63 mmol) and iodobenzene (889 mg, 4.36 mmol) in dioxane (15.0 mL) was added CuI (276 mg, 1.45 mmol), 2-(dimethylamino)acetic acid hydrochloride (101 mg, 7.26 mmol), and cesium carbonate (2.36 g, 7.26 mmol). The resulting mixture was heated to 90° C. and allowed to stir under inert atmosphere for 12 h. Upon completion, the reaction mixture was filtered, concentrated under reduced pressure, and the resulting oil was triturated with methyl-t-butyl ether (10 mL) to afford 23 (700 mg). LCMS (ESI): m/z 324.0 (M+H).

Step 2.

To a solution of 23 (350 mg, 1.08 mmol) and pyridin-3-ol (123 mg, 1.30 mmol) stirred in dioxane (4.0 mL) was added CuI (82 mg, 0.43 mmol), cesium carbonate (703 mg, 2.16 mmol) and 2-(dimethylamino)acetic acid hydrochloride (30 mg, 0.22 mmol). The reaction mixture was stirred at 90° C. under N$_2$ for 12 h. Upon completion, the reaction mixture was filtered and concentrated under reduced pressure. Purification by HPLC (0.04% HCl/CH$_3$CN/H$_2$O system) resulted in Compound 24 (50 mg, 26%). $^1$H NMR (DMSO-d$_6$, 400 MHz) δ 8.59-8.58 (d, 2H), 8.54-8.53 (d, 1H), 8.04-8.02 (m, 1H), 7.47-7.45 (m, 1H), 7.42-7.41 (m, 4H), 7.33-7.31 (m, 1H), 7.28-7.20 (m, 1H), 5.0 (s, 2H); LCMS (ESI): m/z 339.0 (M+H).

Example 25

Synthesis of Compound 25

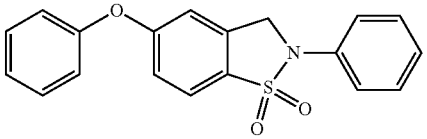 [SMILES: O=S1(=O)c2ccc(Oc3ccccc3)cc2CN1c1ccccc1]

Compound 25 was prepared in a manner similar to Compound 24. $^1$H NMR: (DMSO-d$_6$, 400 MHz) δ 8.00-7.98 (d, 1H), 7.50-7.40 (m, 6H), 7.21-7.17 (m, 6H), 4.99 (s, 2H); LCMS (ESI): m/z 338.0 (M+H).

Example 26

Synthesis of Compound 26

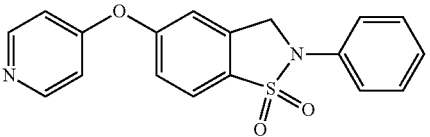

Compound 26 was prepared in a manner similar to Compound 24. $^1$H NMR (DMSO, 400 MHz) δ 8.17-8.15 (d, 1H), 7.81 (s, 1H) 7.74-7.72 (d, 2H), 7.58-7.55 (t, 1H), 7.49-7.48 (m, 4H), 7.24-7.23 (m, 1H), 6.55-6.53 (d, 1H), 6.41-6.38 (t, 1H), 5.11 (s, 2H); LCMS (ESI): m/z 339.0 (M+H).

Example 27

Synthesis of Compound 27

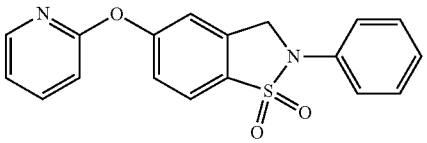 [SMILES: O=S1(=O)c2ccc(Oc3ccccn3)cc2CN1c1ccccc1]

Compound 27 was prepared in a manner similar to Compound 24. $^1$H NMR (DMSO-d$_6$, 400 MHz) δ 8.16-8.14 (d, 1H), 7.74-7.72 (d, 1H), 7.56-7.55 (d, 1H), 7.49-7.48 (m, 3H), 6.55-6.53 (d, 1H), 6.41-6.39 (m, 1H), 5.11 (s, 2H); LCMS (ESI): m/z 339.0 (M+H).

Example 28

Synthesis of Compound 28

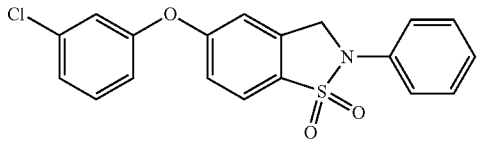 [SMILES: O=S1(=O)c2ccc(Oc3cccc(Cl)c3)cc2CN1c1ccccc1]

Compound 28 was prepared in a manner similar to Compound 24. $^1$H NMR (DMSO-d$_6$ 400 MHz) δ 8.03-8.01 (d, 1H), 7.51-7.41 (m, 8H), 7.34-7.18 (m, 3H), 5.01 (s, 2H); LCMS (ESI): m/z 372.0 (M+H).

Example 29

Synthesis of Compound 29

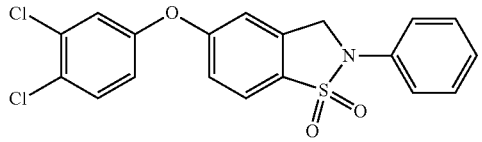 [SMILES: O=S1(=O)c2ccc(Oc3ccc(Cl)c(Cl)c3)cc2CN1c1ccccc1]

Compound 29 was prepared in a manner similar to Compound 24. $^1$H NMR (DMSO-d$_6$ 400 MHz) δ 8.03-8.01 (d, 1H), 7.75-7.72 (d, 1H), 7.58 (s, 1H), 7.48-7.29 (m, 4H), 7.23-7.20 (m, 4H), 5.00 (s, 2H); LCMS (ESI): m/z 405.9 (M+H).

Example 30

Synthesis of Compound 30

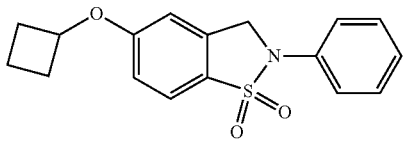 [SMILES: O=S1(=O)c2ccc(OC3CCC3)cc2CN1c1ccccc1]

Compound 30 was prepared in a manner similar to Compound 24. $^1$H NMR (DMSO-d$_6$ 400 MHz) δ 7.88-7.86 (d, 1H), 7.48-7.41 (m, 4H), 7.20-7.16 (m, 1H), 7.20-7.16 (m, 2H), 4.96-4.87 (d, 2H), 4.83-4.80 (m, 1H), 2.41-2.11 (m, 2H), 2.09-2.04 (m, 2H), 1.83-1.81 (m, 1H), 1.71-1.64 (m, 1H); LCMS (ESI): m/z 316.0 (M+H).

Example 31

Synthesis of Compound 31

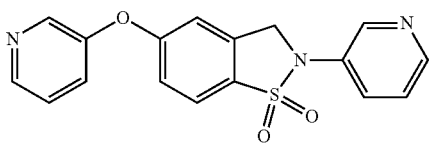 [SMILES: O=S1(=O)c2ccc(Oc3cccnc3)cc2CN1c1cccnc1]

Compound 31 was prepared in a manner similar to Compound 24. $^1$H NMR (DMSO-d$_6$, 400 MHz) δ 8.71-8.69 (d, 2H), 8.61-8.60 (d, 2H), 8.15-8.13 (d, 2H), 7.90-7.88 (m, 1H), 7.72-7.37 (m, 2H), 5.17 (s, 2H); LCMS (ESI): m/z 340.0 (M+H).

Example 32

Synthesis of Compound 32

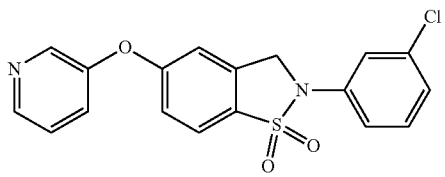 [SMILES: O=S1(=O)c2ccc(Oc3cccnc3)cc2CN1c1cccc(Cl)c1]

Compound 32 was prepared in a manner similar to Compound 24. $^1$H NMR (DMSO-d$_6$ 400 MHz) δ 8.57-8.54 (d, 2H), 8.07-8.05 (d, 1H), 7.72-7.59 (d, 1H), 7.48-7.42 (d, 1H), 7.40-7.38 (m, 1H), 7.33-7.26 (m, 2H), 5.05 (s, 2H); LCMS (ESI): m/z 373.0 (M+H).

Example 33

Synthesis of Compound 33

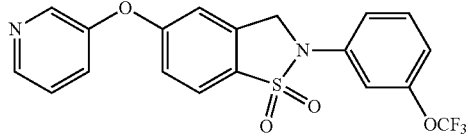 [SMILES: O=S1(=O)c2ccc(Oc3cccnc3)cc2CN1c1cccc(OC(F)(F)F)c1]

Compound 33 was prepared in a manner similar to Compound 24. $^1$H NMR (DMSO-d$_6$ 400 MHz) δ 8.57-8.53 (d, 1H), 8.08-8.06 (d, 1H), 7.60-7.58 (m, 1H), 7.45-7.26 (m, 2H), 5.07 (s, 2H); LCMS (ESI): m/z 423.0 (M+H).

Example 34

Synthesis of Compound 34

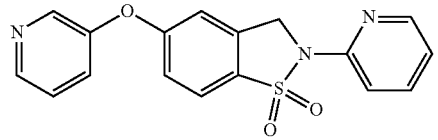 [SMILES: O=S1(=O)c2ccc(Oc3cccnc3)cc2CN1c1ccccn1]

Compound 34 was prepared in a manner similar to Compound 24. $^1$H NMR (DMSO-d$_6$, 400 MHz) δ 8.58-8.48 (m, 2H), 8.42 (d, 1H), 8.06 (d, 1H), 7.93-7.86 (m, 1H), 7.70 (dd, 1H), 7.55 (dd, 1H), 7.37-7.29 (m, 3H), 7.17 (dd, 1H), 5.12 (s, 2H); LCMS (ESI): m/z 340.0 (M+H).

Example 35

Synthesis of Compound 35

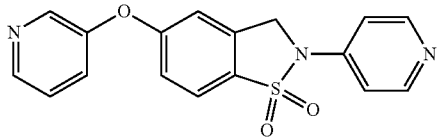 [SMILES: O=S1(=O)c2ccc(Oc3cccnc3)cc2CN1c1ccncc1]

Compound 35 was prepared in a manner similar to Compound 24. ¹H NMR (DMSO-d₆ 400 MHz) δ 8.82 (s, 1H), 8.72-8.70 (d, 3H), 8.22-8.14 (d, 1H), 8.01-8.00 (d, 1H), 7.99-7.86 (m, 1H), 7.86-7.83 (d, 2H), 5.28 (s, 2H); LCMS (ESI): m/z 340.0 (M+H).

Example 36

Synthesis of Compound 36

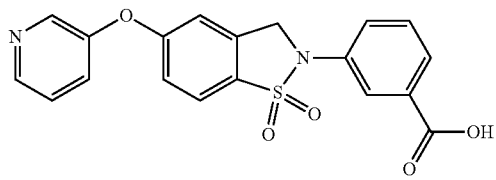 [SMILES: O=C(O)c1cccc(N2Cc3cc(Oc4cccnc4)ccc3S2(=O)=O)c1]

Compound 36 was prepared in a manner similar to Compound 24. ¹H NMR (CD₃OD 400 MHz) δ 8.81 (s, 1H), 8.68-8.67 (d, 1H), 8.28-8.11 (d, 1H), 8.06-8.00 (m, 2H), 7.88-7.86 (d, 1H), 7.56-7.48 (d, 1H), 5.03 (s, 2H); LCMS (ESI): m/z 383.0 (M+H).

Example 37

Synthesis of Compound 37

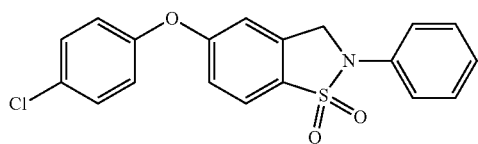 [SMILES: O=S1(=O)c2ccc(Oc3ccc(Cl)cc3)cc2CN1c1ccccc1]

Compound 37 was prepared in a manner similar to Compound 24. ¹H NMR (CD₃OD, 400 MHz) δ 7.85-7.83 (d, 1H), 7.48-7.40 (m, 5H), 7.20-7.17 (m, 4H), 7.15-6.85 (m, 1H), 4.560 (s, 2H); LCMS (ESI): m/z 372.0 (M+H).

Example 38

Synthesis of Compound 38

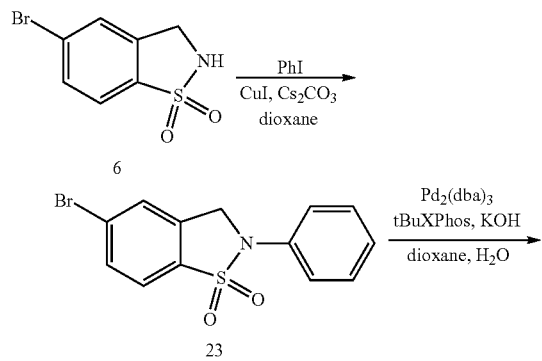

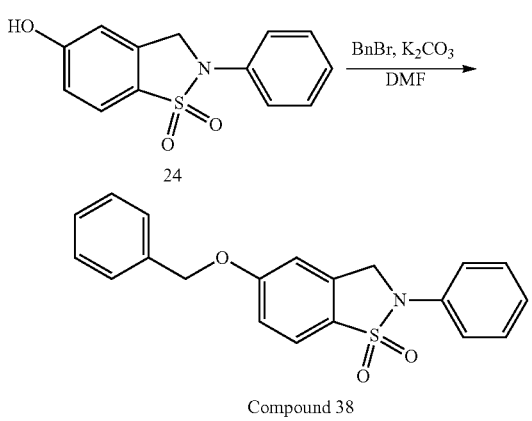

Step 1.

To a mixture of 6 (500 mg, 2.02 mmol) and iodobenzene (453 mg, 2.22 mmol) in dioxane (10 mL) was added CuI (39 mg, 0.20 mmol) N1,N2-dimethylethane-1,2-diamine (35.6 mg, 0.40 mmol), K₃PO₄ (858 mg, 4.04 mmol). The mixture was heated to 100° C. and stirred for 12 hours. The reaction mixture was poured into water (20 mL) and extracted with ethyl acetate (3×20 mL). The organic phase was washed with brine (2×20 mL), dried over anhydrous Na₂SO4, filtered and concentrated under reduced pressure. The residue was purified by prep-TLC (petroleum ether/ethyl acetate)=1:1 to afford 23 (250 mg, 0.66 mmol, 33%) as a white solid.

Step 2.

To a mixture of 23 (80 mg, 0.25 mmol) and KOH (69 mg, 1.23 mmol) in dioxane (1.0 mL) and H₂O (1.0 mL) was added Pd₂(dba)₃ (22.6 mg, 0.025 mmol), t-BuXphos (11 mg, 0.025 mmol) in one portion at 25° C. under N₂. The mixture was heated to 100° C. and stirred for 12 hours and then quenched with 1 N HCl (to pH=6). The reaction mixture was extracted with EtOAc (3×5 mL), and the organic phase was dried over Na₂SO₄, filtered and concentrated under reduced pressure to provide 24 (35 mg) which was used directly in the next step without purification.

Step 3.

To a solution of 24 (15 mg, 0.057 mmol) and bromomethylbenzene (9.8 mg, 0.057 mmol) stirred in DMF (2.0 mL) was added K₂CO₃ (56 mg, 0.17 mmol). The reaction mixture was stirred at 90° C. for 12 h under N₂. When LCMS showed the reaction was complete, the reaction mixture was concentrated to afford the crude product. Purification by prep-HPLC afforded Compound 38 (3 mg). ¹H NMR (DMSO-d₆, 400 MHz) δ 7.91-7.49 (d, 1H), 7.48-7.44 (m, 9H), 7.40-7.38 (d, 1H), 5.26 (s, 2H), 4.99 (s, 2H); LCMS (ESI): m/z 352.0 (M+H).

Example 39

Synthesis of Compound 39

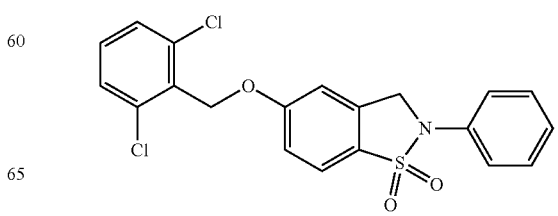

Compound 39 was prepared in a manner similar to Compound 38. $^1$H NMR (DMSO-$d_6$, 400 MHz) δ 7.95-7.93 (d, 1H), 7.61-7.59 (d, 2H), 7.59-7.51 (m, 6H), 7.49-7.45 (d, 1H), 7.35-7.19 (m, 1H), 5.38 (s, 2H), 5.03 (s, 2H); LCMS (ESI): m/z 420.0 (M+H).

Example 40

Synthesis of Compound 40

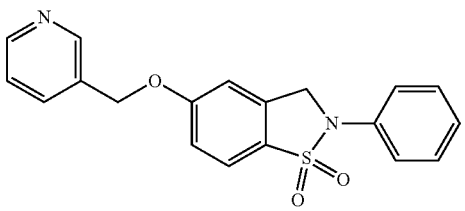 [SMILES: O=S1(=O)c2ccc(OCc3cccnc3)cc2CN1c1ccccc1]

Compound 40 was prepared in a manner similar to Compound 38. $^1$H NMR (DMSO-$d_6$, 400 MHz) δ 8.24-8.22 (d, 1H), 7.96-7.94 (d, 1H), 7.74 (s, 1H), 7.48-7.45 (m, 4H), 7.34-7.22 (m, 3H), 7.19-7.17 (m, 1H), 5.39 (s, 2H), 5.01 (s, 2H); LCMS (ESI): m/z 353.0 (M+H).

Example 41

Synthesis of Compound 41

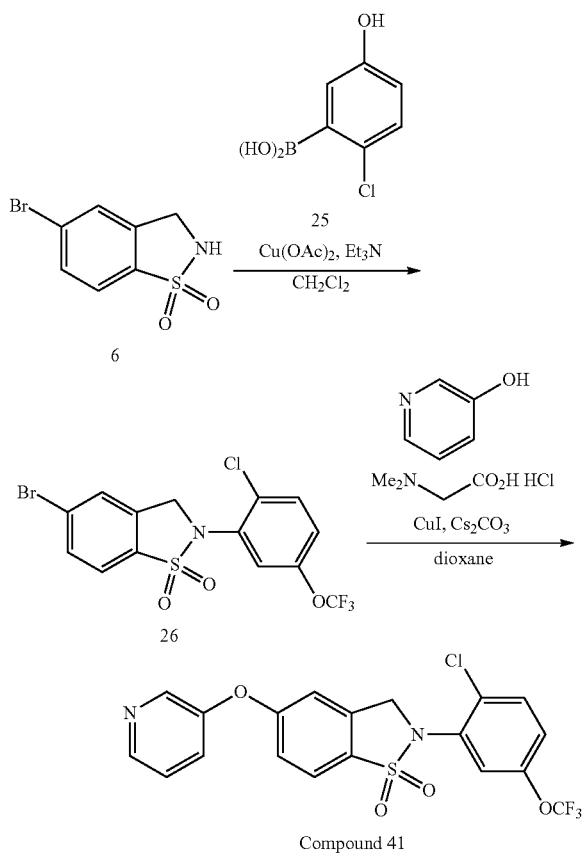

Step 1.

A mixture of 6 (120 mg, 0.48 mmol), 25 (140 mg, 0.58 mmol), Cu(OAc)$_2$ (88 mg, 0.48 mmol), Et$_3$N (98 mg, 0.97 mmol) and 4A molecular sieves (250 mg) in CH$_2$Cl$_2$ (10.0 mL) was degassed and purged with O$_2$ (3×). After stirring for 1 h at 15° C. for 1 hour, the reaction mixture was filtered, diluted with water (20 mL), and extracted with CH$_2$Cl$_2$ (3×20 mL). The organic layer was washed with brine (2×20 mL), dried over anhydrous Na$_2$SO$_4$, filtered and concentrated under reduced pressure to give 26 (220 mg) as a yellow solid which was used directly in the next step without further purification.

Step 2.

A mixture of 26 (220 mg, crude material), pyridine-3-ol (48 mg, 0.51 mmol), CuI (32 mg, 0.17 mmol), N,N-dimethylglycine hydrochloride (12 mg, 0.084 mmol) and Cs$_2$CO$_3$ (275 mg, 0.084 mmol) in dioxane (3.0 mL) was degassed and purged with N$_2$ (3×). The mixture was stirred at 100° C. for 12 hours and then filtered. The filtrate was concentrated under reduced pressure to give a residue, which was purified by prep-HPLC to afford Compound 41 (2.6 mg, 1%) as a white solid. $^1$H NMR (CD$_3$OD, 400 MHz) δ 8.80 (s, 1H), 8.66 (s, 1H), 8.26-8.24 (d, 1H), 8.02-7.99 (d, 2H), 7.74-7.72 (d, 1H), 7.67 (s, 1H), 7.49-7.44 (m, 3H), 4.95 (s, 2H); LCMS (ESI): m/z 457.0 (M+H).

Example 42

Synthesis of Compound 42

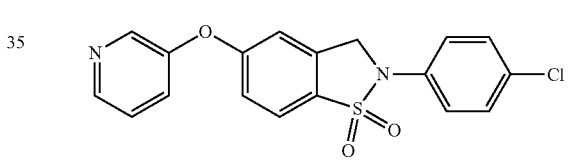

Compound 42 was prepared in a manner similar to Compound 41. $^1$H NMR (400 MHz, CD$_3$OD) δ 8.37 (d, J=8.53 Hz, 1H), 8.16 (s, 1H), 8.03 (d, J=9.04 Hz, 1H), 7.56-7.38 (m, 7H), 4.99 (s, 2H); LCMS (ESI): m/z 457.0 (M+H).

Example 43

Synthesis of Compound 43

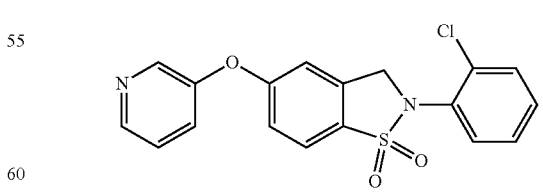

Compound 43 was prepared in a manner similar to Compound 41. $^1$H NMR (400 MHz, CD$_3$OD) δ 7.93 (d, J=8.38 Hz, 1H), 7.86 (d, J=7.94 Hz, 2H), 7.73-7.57 (m, 2H), 7.50-7.32 (m, 3H), 7.29 (s, 1H), 4.88 (s, 2H); LCMS (ESI): m/z 457.0 (M+H).

Example 44

Synthesis of Compound 44

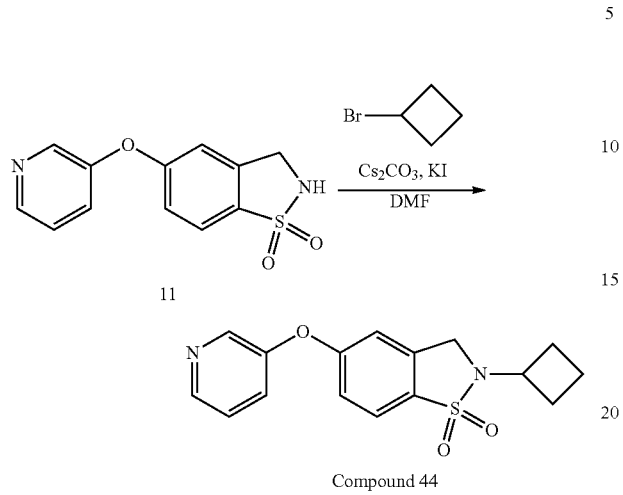

A mixture of 11 (40 mg, 0.15 mmol), bromocyclobutane (103 mg, 0.76 mmol), KI (25 mg, 0.15 mmol), Cs$_2$CO$_3$ (99 mg, 0.31 mmol) in DMF (2.0 mL) was degassed and purged with N$_2$ (3×). The reaction mixture was stirred at 50° C. for 12 hours under N$_2$ atmosphere and then quenched with H$_2$O (10 mL). The solution was extracted with ethyl acetate (2×10 mL) and the combined organic layer was washed with brine (2×10 mL), dried over sodium sulfate, filtered and concentrated under reduced pressure. Purification by prep-HPLC provided Compound 44 (33 mg, 59%) as a slight yellow solid. $^1$H NMR (DMSO-d$_6$, 400 MHz) δ 8.61 (d, 1H), 8.55 (d, 1H), 7.89 (d, 1H), 7.80 (d, 1H), 7.64 (dd, 1H), 7.31-7.22 (m, 2H), 4.43 (s, 2H), 4.05 (m, 1H), 2.37-2.24 (m, 2H), 2.22-2.11 (m, 2H), 1.78 (m, 2H); LCMS (ESI): m/z 317.1 (M+H).

Example 45

Synthesis of Compound 45

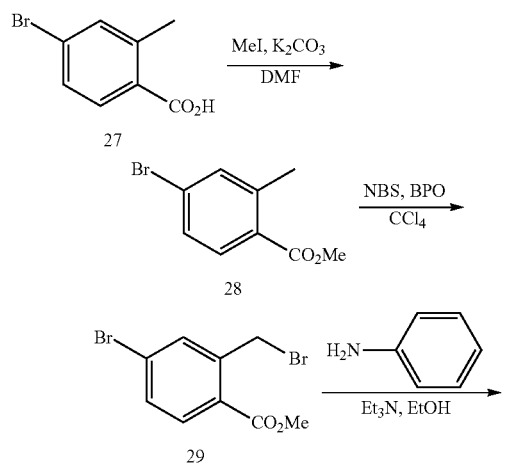

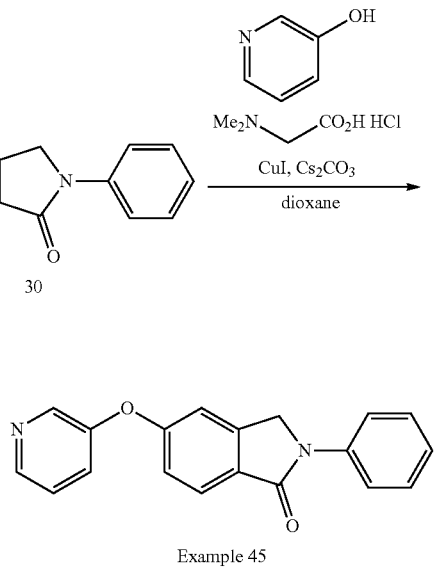

Step 1.

To 27 (3.0 g, 14.0 mmol) and CH$_3$I (3.96 g, 27.9 mmol) in DMF (30 mL) was added K$_2$CO$_3$ (2.89 g, 20.9 mmol). The reaction mixture was stirred at 25° C. for 12 h and then quenched with H$_2$O (20 mL). The solution was extracted with ethyl acetate (3×100 mL) and the organic layer was washed with H$_2$O (3×100 mL) and concentrated to afford 28 (2.9 g, 82%).

Step 2.

To a solution of 28 (1.0 g, 4.37 mmol) and NBS (0.93 g, 5.24 mmol) in CCl$_4$ (10 mL) was added BPO (106 mg, 0.44.00 mmol). The reaction mixture was stirred at 80° C. for 5 h. Upon completion, the reaction was quenched with H$_2$O (10 mL) and extracted with ethyl acetate (3×20 mL). The the organic layer was washed with H$_2$O (3×10 mL), concentrated, and purified by prep-TLC (petroleum:ethyl acetate=20:1) to afford 29 (610 mg, 41%).

Step 3.

To a solution of 29 (500 mg, 1.62 mmol) and aniline (166 mg, 1.78 mmol) in EtOH (2 mL) was added diisopropylethylamine (230 mg, 1.78 mmol). The reaction mixture was stirred at 90° C. for 12 h, cooled to 0° C., and then filtered. The crude material was washed with EtOH to afford 30 (400 mg, 77%) as a white solid without further purification.

Step 4.

To a solution of 30 (120 mg, 0.42 mmol) and pyridin-3-ol (59 mg, 0.62 mmol) in dioxane (2 mL) was added Cs$_2$CO$_3$ (407 mg, 1.25 mmol), CuI (32 mg, 0.17 mmol) and 2-(dimethylamino)acetic acid hydrochloride (23 mg, 0.17 mmol). The reaction mixture was stirred at 110° C. under N$_2$ for 12 h and then filtered and concentrated. Purification by prep-HPLC afforded Compound 45 (100 mg, 72%). $^1$H NMR (DMSO-d$_6$, 400 MHz) δ 8.71 (s, 1H), 8.71-8.62 (d, 1H), 7.98-7.96 (d, 1H), 7.88-7.84 (m, 4H), 7.46-7.40 (m, 3H), 7.31-7.29 (m, 1H), 7.18 (m, 1H), 5.00 (s, 2H); LCMS (ESI): m/z 303.1 (M+H).

Example 46

Synthesis of Compound 46

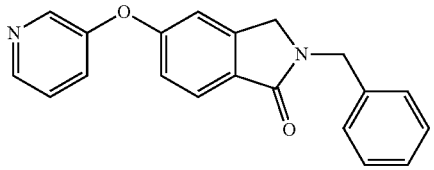 [SMILES: O=C1c2ccc(Oc3cccnc3)cc2CN1Cc1ccccc1]

Compound 46 was prepared in a manner similar to Compound 45. $^1$H NMR (DMSO-$d_6$, 400 MHz) δ 8.83-8.59 (m, 2H), 7.99 (d, 1H), 7.87-7.76 (m, 2H), 7.38-7.32 (m, 3H), 7.31-7.25 (m, 4H), 4.72 (s, 2H), 4.35 (s, 2H); LCMS (ESI): m/z 317.1 (M+H).

BIOLOGICAL EXAMPLES

Example 47

Human GPR120 β-Arrestin Recruitment Assay

This in vitro assay tests compounds' ability to activate intracellular signaling via β-Arrestin recruitment to heterologously expressed human GPR120. This functional cellular assay utilizes enzyme fragment complementation with β-galactosidase (β-gal) as a functional reporter (DiscoveRx PathHunter® β-Arrestin assay platform). The human GPR120 receptor (GenBank accession Number NM_181745) was fused in frame with the small enzyme fragment ProLink™ and co-expressed in CHO-K1 cells with a fusion protein of β-Arrestin 2 and the larger, N-terminal deletion mutant of β-gal. Activation by a GPR120 agonist stimulates binding of β-arrestin to the ProLink-tagged GPCR and forces complementation of the two enzyme fragments, resulting in the formation of an active β-gal enzyme. This interaction leads to an increase in enzyme activity that can be measured using chemiluminescent PathHunter® Detection Reagents.

One day prior to the assay, cells were seeded in a total volume of 20 μl of growth medium into white walled 384-well microplates and incubated at 37° C./5% $CO_2$ overnight. On the day of the assay, growth medium was removed and 20 μl assay buffer (HBSS+10 mM HEPES+ 0.1% heat-inactivated BSA) were added to each well.

Test compounds were dissolved in 100% DMSO to a concentration of 10 mM to provide stock solutions. Serial dilutions were performed from stock solutions into assay buffer to obtain intermediate concentrations of 5-fold higher than the concentrations to be tested. 5 μl of the 5× compound solutions were added to the cells and the assay plates were incubated at 37° C. for 90 minutes. The final concentration of compounds tested in the assay ranged from 1.5 nM to 100 μM. Following incubation, 12.5 μl of PathHunter® detection reagent were added to each well, and plates were incubated at room temperature for 60 minutes. Chemiluminescence was read using an EnVision plate reader (PerkinElmer), raw data were expressed as relative light units (RLU).

To determine agonist potencies ($EC_{50}$ values), non-linear least-squares curve fits of the raw data (RLU) were performed in the GraphPad Prism software package, using the 4-parameter model with variable Hill Slope:

$$Y = \text{Bottom} + \frac{\text{Top} - \text{Bottom}}{1 + 10^{((logEC50-x)*HillSlope)}}$$

Reported below in Table 1 are $pEC_{50}$ values ($pEC_{50}$=−log($EC_{50}$) from curve fit) for compounds of Formula I in this assay, β-Arr pEC50.

Example 48

Human GPR120 Calcium-Release Assay

This in vitro assay tests compounds' ability to activate heterologously expressed human GPR120 via G-protein coupling leading to generation of inositol 1,4,5-triphosphate and mobilization of intracellular calcium. This functional cellular assay is based on the luminescence of mitochondrial aequorin following intracellular $Ca^{2+}$ release. Aequorin is a photoprotein isolated from the jellyfish *Aequorea victoria*. The active protein is formed in the presence of molecular oxygen from apoaequorin and its cofactor coelenterazine. Binding of $Ca^{2+}$ to the active protein induces a conformational change, resulting in oxidation of coelenterazine and subsequent blue luminescence.

The short variant of the human GPR120 receptor (GenBank accession Number AAI01176) was stably expressed in a CHO-K1 cell line coexpressing Gα16 and mitochondrial apoaequorin.

Cells were grown to mid-log phase in culture media without antibiotics, were detached with PBS/EDTA, centrifuged and resuspended in assay buffer (DMEM-F12 medium with 15 mM HEPES pH 7.0 and 0.1% protease free BSA) at a concentration of $10^6$ cells/mL. Cells were incubated at room temperature for at least 4 hours with 5 μM coelenterazine h.

Test compounds were dissolved in 100% DMSO to a concentration of 20 mM to provide stock solutions. Serial dilutions were performed from stock solutions in 100% DMSO to obtain intermediate concentrations 200-fold higher than the concentrations to be tested. Each sample was diluted 100-fold into assay buffer. 50 μl of these compound solutions were dispensed into each well of 96-well assay plates. The final concentration of compounds tested in the assay ranged from 5 nM to 100 μM. α-Linolenic acid was used as a reference compound. Each test was performed in duplicate.

To start the assay, 50 μl of cell suspension were added to each well of the assay plate. The resulting luminescence was recorded using a Hamamatsu Functional Drug Screening System 6000 (FDSS 6000), and raw data were expressed as relative light units (RLU).

To determine agonist potencies ($EC_{50}$ values), non-linear least-squares curve fits of the raw data (RLU) were performed in the GraphPad Prism software package, using the 4-parameter model with variable Hill Slope:

$$Y = \text{Bottom} + \frac{\text{Top} - \text{Bottom}}{1 + 10^{((logEC50-x)*HillSlope)}}$$

Reported below in Table 1 are $pEC_{50}$ values ($pEC_{50}$=−log($EC_{50}$) from curve fit) for representative compounds of Formula I in this assay, Ca2+ pEC50.

TABLE 1

Activity of compounds of Formula I in in vitro assays.

| Compound # | β-Arr pEC50 | Ca2+ pEC50 |
|---|---|---|
| 1 | 5.7 | 6.2 |
| 2 | 6.3 | 6 |
| 3 | 6.8 | 5.4 |
| 4 | 6.6 | 5.1 |
| 5 | 5.8 | |
| 6 | <5.0 | |
| 7 | 5.4 | 5.7 |
| 8 | 5.2 | |
| 9 | 5.9 | 5.8 |
| 10 | 5.5 | 5.6 |
| 11 | 5.1 | 5.4 |
| 12 | <4.5 | |
| 13 | <5.0 | |
| 14 | 4.9 | 4.7 |
| 15 | 6.3 | 6.1 |
| 16 | 5.5 | |
| 17 | <5.0 | |
| 18 | <5.0 | |
| 19 | 5.1 | 4.8 |
| 20 | 5.5 | 5 |
| 21 | <4.5 | |
| 22 | <4.5 | |
| 23 | 5.7 | |
| 24 | 5.1 | 5.6 |
| 25 | 6 | 5.9 |
| 26 | <4.5 | |
| 27 | <4.5 | |
| 28 | 6.1 | 4.4 |
| 29 | <4.5 | <4.0 |
| 30 | 5.6 | <4.0 |
| 31 | <5.0 | |
| 32 | 5.8 | |
| 33 | 5.3 | |
| 34 | 4.8 | 5 |
| 35 | 4.9 | |
| 36 | <5.0 | |
| 37 | <5.0 | |
| 38 | 5.3 | |
| 39 | 5 | |
| 40 | <4.5 | |
| 41 | <4.5 | |
| 42 | 5.4 | |
| 43 | <5.0 | |
| 44 | 4.9 | |
| 45 | <5.0 | |
| 46 | 5.2 | 5 |

The results above show that the compounds of the invention, as illustrated in the examples above and generally as defined by Formula 1, are potent GRP120 agonists that will find application in the treatment of T2D. While, as disclosed in the detailed description above, these compounds can be administered via any route of administration and at various frequencies, in one preferred embodiment, they are administered once a day to T2D patients for treatment and control of that condition in the form of a tablet or capsule, taken orally.

Example 49

Biological Example: GPR120 C57BL/6J Mouse Oral Glucose Tolerance Test

An oral glucose tolerance test (OGTT) was performed with certain compounds to determine their acute effect on glucose excursions.

Male C57BL/6J mice aged 8-10 weeks and kept on a regular chow diet were used for the study, 10 Mice were used per treatment group, with individual mice weighing in the range of 24-30 grams on study day, and a mean weight of 27.2-27.3 grams for each treatment group.

Test articles were prepared as suspensions in dosing vehicle (0.5% hydroxypropyl methylcellulose and 2% Tween-20 in water) at a concentration of 10 mg/mL by mixing and sonication.

The mice were fasted for 6 hours prior to dosing of vehicle or test articles at 100 mg/kg (10 mL/kg) by oral gavage. Glucose was dosed (PO) at 3 g/kg 30 min after dosing of test articles. Animals were bled via tail snip to determine basal glucose levels 30 min prior to the glucose challenge, and again at 0, 15, 30, 60, 90 and 120 minutes following the glucose challenge. A Johnson & Johnson OneTouch Glucometer was used to determine glucose levels in all blood samples.

Glucose values were entered into an Excel sheet, and mean values±standard error of the mean were graphed in GraphPad Prism. Significance of difference between groups was analyzed by performing two-way RM ANOVA for the time course study. P values less than 0.05 were considered statistically significant.

Example 50

Anti-Inflammatory Activity in LPS-Stimulated Human Peripheral Blood Mononuclear Cells The ability of compounds of this invention to inhibit TNFα production was assessed by using human peripheral blood mononuclear cells (hPBMC) which synthesize and secrete TNFα when stimulated with lipopolysaccharide (LPS).

Mononuclear Cell packs collected by and purchased from Key Biologics were used for the preparation of hPBMC. Briefly, cell product was sterilely removed from the phoresis bag, carefully layered onto pre-warmed Ficoll (Histopaque 1077) and centrifuged at 1,800×g for 15 minutes at room temperature with the brake off. Following centrifugation, the interface was removed and added to sterile Dulbecco's Phosphate Buffered Saline (DPBS). The cells were then pelleted at 300×g for ten minutes at room temperature. The cells were resuspended in fresh DPBS then repelleted to minimize platelet contamination. The subsequent pellet was resuspended in DPBS and the cells counted. Cells were repelleted and then cryopreserved at $1 \times 10^8$ cells per ml in DMEM/30% FBS/10% DMSO. For all hPBMC preparations, individual donors were kept separate throughout the entire process. For the assay, hPBMC were seeded into flat-bottom 96-well plates at 500,000 cells/well in 80 µl assay medium (DMEM, 0.1% FBS, 1% penicillin/streptomycin) and allowed to recover in a 37° C. incubator for one hour before the addition of compounds.

Compounds were solubilized from powder as 20 mM stocks with 100% DMSO and then serially diluted into assay medium to prepare 10× stocks to achieve five concentrations (100 µM, 30 µM, 10 µM, 3 µM and 1 µM) in the assay. All compound dilutions were added to the plates containing hPBMC (10 µl in final assay volume of 100 µl) and incubated at 37° C. for an hour before the addition of stimulus. Control wells received 10 µl vehicle (media containing 5% DMSO).

For the LPS challenge, a 1 mg/ml stock solution of lipopolysaccharide (LPS) was diluted 1000-fold into assay medium (10 µl LPS+10 ml media). All wells except the "Unstimulated" control wells received 10 µl of LPS. The "Unstimulated" control wells received 10 µl media. The plates were incubated for 4 hours at 37° C. After 4 hours, the plates were centrifuged at 1,200 rpm for 5 minutes and culture media supernatants were collected into fresh 96-well plates.

TNFα levels in culture supernatants were determined by immunoassay using the Meso Scale Diagnostics electrochemiluminescent immunoassay system. Meso Scale V-plex 96-well plates (Meso Scale Diagnostics, Rockville, MD) were used for detection of TNFα as directed by the manufacturer (overnight incubation protocol). Samples were diluted 100-fold. TNFα concentrations were determined by interpolating against a standard curve and then multiplying by 100 to arrive at "pg/ml" values. TNFα release was reported as % of vehicle treated LPS stimulated cells.

While certain embodiments have been illustrated and described, it will be understood that changes and modifications can be made therein in accordance with ordinary skill in the art without departing from the present invention in its broader aspects as defined in the following claims.

REFERENCES

1. Data for diabetes: World Health Organization, Fact Sheet No. 312 (http://www.who.int/mediacentre/factsheets/fs312/en/)
2. Hirasawa et al. *Nat. Med.* 2005, 11:90-94.
3. Oh et al. *Cell* 2010, 142:687-698.
4. Ichimura et al. *Nature* 2012, 483:350-354.
5. Cornall et al. *Drug Disc. Today* 2014, 19:670-679.
5a. Nobili et al. *PLOS one* 2014, 9: e88005.
6a. Wellhauser et al. *J Neuroinflamm* 2014, 11: 60.
7a. Dragano et al. *J Neuroinflamm* 2017, 17:91.
8a. Heneka et al. *Nature* 2013, 493: 674.
9a. Yan et al. *Immunity* 2013, 38: 1154.
10a. Tan et al. *Cell Death Dis* 2014, 5: e1382.
11a. Kaushal et al. *Cell Death Differentiation* 2015, 22: 1676.
6. Suzuki et al. *J. Med. Chem.* 2008, 51:7640-7644.
7. Hara et al. *Naunyn Schmied. Arch. Pharmacol.* 2009, 380:247-255.
8. Shimpukade et al. *J. Med. Chem.* 2012, 55:4511-4515.
9. Hudson et al. *Mol Pharmacol.* 2013, 84:710-725.
10. Oh et al. *Nat. Med.* 2014, 20:942-947.
11. Sparks et al. *Bioorg. Med. Chem. Lett.* 2014, 24:3100-3103.
12. Tanaka et al. *Naunyn-Schmiedeberg's Arch Pharmacol.* 2008, 377:523-527.
13. Lu et al. *Am. J. Gastrointest. Liver Physiol.* 2012, 303:G367-G376.
14. Suckow et al. *J. Bio. Chem.* 2014, 289: 15751-15763.
15. US 20080167378
16. WO 2008066131
17. WO 2008103501
18. WO 2008139987
19. WO 2009147990
20. US 20100130559
21. WO 2010048207
22. WO 2010080537
23. WO 2011159297
24. US 20110313003
25. WO2013139341
26. WO 2014069963
27. US 20140275172
28. US 20140275179
29. WO 20140275182
30. WO 2014059232
31. WO 2014159794
32. US 20140275173
33. WO 2010104195

The invention claimed is:

1. A compound of formula:

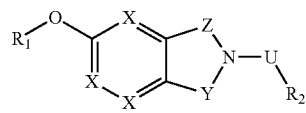

wherein
each X independently is CH, CR$_3$, or N;
Y is SO$_2$;
Z is —CH$_2$—, —CH(CH$_3$)—, —C(CH$_3$)$_2$—, —C(CH$_2$CH$_2$)—(cyclopropano), CO, —(CO)CH$_2$—, —CH$_2$CH$_2$—, or —CHCH—;
U is a covalent bond, CH$_2$, —CH(CH$_3$)—, —C(CH$_3$)$_2$—, or —CH$_2$CH$_2$—;
R$_1$ is an optionally substituted 3-7 membered cycloalkyl or heterocyclyl group;
R$_2$ is an optionally substituted 3-7 membered cycloalkyl or heterocyclyl group, an optionally substituted 6-membered aryl group, an optionally substituted 5- or 6-membered heteroaryl group, an optionally substituted 5,6- or 6,6-membered bicyclic aryl or heteroaryl group, or an optionally substituted bicyclic aryl group; and
R$_3$ is a halogen, or an optionally substituted alkyl or alkoxy group.

2. The compound of claim 1 of formula

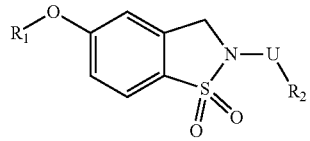

wherein
U is a covalent bond, CH$_2$, —CH(CH$_3$)—, —C(CH$_3$)$_2$—, or —CH$_2$CH$_2$—;
R$_1$ is an optionally substituted 3-7 membered cycloalkyl or heterocyclyl group; and
R$_2$ is an optionally substituted 3-7 membered cycloalkyl or heterocyclyl group, an optionally substituted 6-membered aryl group, an optionally substituted 5- or 6-membered heteroaryl group, an optionally substituted 5,6- or 6,6-membered bicyclic heteroaryl group, or an optionally substituted bicyclic aryl group.

3. A compound of the structure

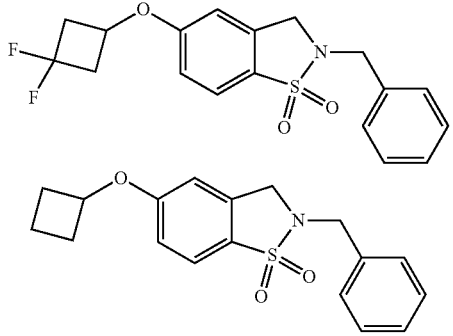

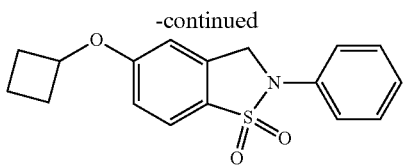

or a tautomer thereof, or an isotopomer thereof, or a stereoisomer thereof, or a pharmaceutically acceptable salt of each thereof, or a prodrug thereof, or a pharmaceutically acceptable solvate of each of the foregoing.

4. A pharmaceutical composition comprising a compound of claim 1 and a pharmaceutically acceptable excipient.

5. A method for agonizing GPR120, comprising contacting the GPR120 with a compound of claim 1.

6. A method for modulating metabolism in a mammal, comprising contacting GPR120 in the mammal with an amount of the compound of claim 1 effective to modulate metabolism in the mammal.

7. A method for modulating metabolism in a mammal, comprising administering to the mammal an amount of the composition of claim 4 effective to modulate metabolism in the mammal.

8. A method for reducing inflammation in a mammal, comprising contacting GPR120 in the mammal with an amount of the compound of claim 1 effective to reduce the inflammation.

9. A method for reducing inflammation in a mammal, comprising administering to the mammal an amount of the composition of claim 4 effective to reduce the inflammation.

10. A method for reducing neuroinflammation in a mammal, comprising contacting GPR120 in the mammal with an amount of the compound of claim 1 effective to reduce the neuroinflammation.

11. A method for reducing neuroinflammation in a mammal, comprising administering to the mammal an amount of the composition of claim 4 effective to reduce neuroinflammation.

12. A method for treating diabetes, pre-diabetes or metabolic syndrome, or one or more symptoms of each thereof in a mammal, comprising contacting GPR120 in the mammal with a therapeutically effective amount of the compound of claim 1.

13. A method for treating diabetes, pre-diabetes or metabolic syndrome, or one or more symptoms of each thereof in a mammal, comprising administering to the mammal a therapeutically effective amount of the composition of claim 4.

14. A method for treating steatohepatitis in a mammal, comprising contacting GPR120 in the mammal with a therapeutically effective amount of the compound of claim 1.

15. A method for treating steatohepatitis in a mammal, comprising administering to the mammal a therapeutically effective amount of the composition of claim 4.

16. A method for treating non-alcoholic steatohepatitis in a mammal, comprising contacting GPR120 in the mammal with a therapeutically effective amount of the compound of claim 1.

17. A method for treating non-alcoholic steatohepatitis in a mammal, comprising administering to the mammal a therapeutically effective amount of the composition of claim 4.

18. A method for treating a disorder associated with, leading to, or resulting from neuroinflammation in a mammal, comprising contacting GPR120 in the mammal with a therapeutically effective amount of the compound of claim 1.

19. A method for treating a disorder associated with leading to, or resulting from neuroinflammation in a mammal, comprising administering to the mammal a therapeutically effective amount of the composition of claim 4.

20. A method for treating Alzheimer's disease, Parkinson's disease, frontotemporal dementia, amyotrophic lateral sclerosis or multi-system atrophy, or one or more symptoms of each thereof, comprising contacting GPR120 in the patient with a therapeutically effective amount of the compound of claim 1.

* * * * *